(12) United States Patent
Chu et al.

(10) Patent No.: US 11,147,619 B2
(45) Date of Patent: Oct. 19, 2021

(54) METHODS AND DEVICES FOR APPLYING ENERGY TO BODILY TISSUES

(71) Applicant: MicroCube, LLC, Fremont, CA (US)

(72) Inventors: Chun Yiu Chu, Oakland, CA (US); Ketan Shroff, Pleasanton, CA (US); Clarence Emmons, Capitola, CA (US); Amrish J. Walke, Milpitas, CA (US); Dinesh I. Mody, San Jose, CA (US)

(73) Assignee: MicroCube, LLC, Fremont, CA (US)

( * ) Notice: Subject to any disclaimer, the term of this patent is extended or adjusted under 35 U.S.C. 154(b) by 0 days.

(21) Appl. No.: 16/592,305

(22) Filed: Oct. 3, 2019

(65) Prior Publication Data
US 2020/0121388 A1  Apr. 23, 2020

Related U.S. Application Data

(63) Continuation of application No. 15/974,386, filed on May 8, 2018, now Pat. No. 10,470,819, which is a continuation of application No. 12/603,349, filed on Oct. 21, 2009, now Pat. No. 9,993,293.

(60) Provisional application No. 61/162,244, filed on Mar. 20, 2009, provisional application No. 61/113,189, filed on Nov. 10, 2008, provisional application No. 61/113,192, filed on Nov. 10, 2008, provisional application No. 61/113,194, filed on Nov. 10, 2008, provisional application No. 61/162,241, filed on Mar.

(Continued)

(51) Int. Cl.
*A61B 18/18* (2006.01)
*A61B 18/00* (2006.01)
*A61N 5/04* (2006.01)

(52) U.S. Cl.
CPC .......... *A61B 18/18* (2013.01); *A61B 18/1815* (2013.01); *A61B 2018/00982* (2013.01); *A61B 2018/1861* (2013.01); *A61N 5/045* (2013.01)

(58) Field of Classification Search
CPC ............................ A61B 18/18; A61B 18/1815
See application file for complete search history.

(56) References Cited

U.S. PATENT DOCUMENTS

| 4,583,556 A | 4/1986 | Hines et al. |
| 4,658,836 A | 4/1987 | Turner |
| (Continued) | | |

FOREIGN PATENT DOCUMENTS

| EP | 1145686 | 10/2001 |
| JP | 2005-312807 | 11/2005 |
| (Continued) | | |

*Primary Examiner* — Ronald Hupczey, Jr.
(74) *Attorney, Agent, or Firm* — Levine Bagade Han LLP

(57) ABSTRACT

Devices and methods are disclosed for treating tissue with microwave energy. Such devices and methods are able to treat cavities or surface tissue by creating one or more area or volumetric lesions. Also disclosed are flexible, low-profile devices that can be inserted non-invasively or minimally invasively near or into the target tissue as well as microwave antennas designed to generate ablation profiles that can ablate a large area or a large volume of target tissue in a single ablation. The devices include antennas wherein the field profile generated by an antenna is tailored and optimized for a particular clinical application. The antennas use unique properties of microwaves such as interaction of a microwave field with a metallic object and the use of additional shaping elements to shape the microwave field.

7 Claims, 18 Drawing Sheets

Related U.S. Application Data 20, 2009, provisional application No. 61/222,409, filed on Jul. 1, 2009.

(56) References Cited

U.S. PATENT DOCUMENTS

| | | | |
|---|---|---|---|
| 4,700,716 A | 10/1987 | Kasevich et al. | |
| 5,007,437 A | 4/1991 | Sterzer | |
| 5,057,106 A | 10/1991 | Kasevich et al. | |
| 5,129,396 A * | 7/1992 | Rosen | A61B 17/22 |
| | | | 600/407 |
| 5,277,201 A | 1/1994 | Stern | |
| 5,449,380 A | 9/1995 | Chin | |
| 5,603,697 A | 2/1997 | Grundy et al. | |
| 5,741,249 A | 4/1998 | Moss et al. | |
| 5,769,880 A | 6/1998 | Truckai et al. | |
| 5,788,692 A | 8/1998 | Campbell et al. | |
| 5,861,021 A | 1/1999 | Thome et al. | |
| 5,902,251 A | 5/1999 | vanHooydonk | |
| 5,928,145 A | 7/1999 | Ocali et al. | |
| 6,210,367 B1 * | 4/2001 | Carr | A61B 18/18 |
| | | | 604/114 |
| 6,287,302 B1 | 9/2001 | Berube | |
| 6,306,132 B1 * | 10/2001 | Moorman | A61B 10/0233 |
| | | | 600/562 |
| 6,381,483 B1 * | 4/2002 | Hareyama | A61B 5/055 |
| | | | 600/407 |
| 6,471,696 B1 | 10/2002 | Berube et al. | |
| 6,503,247 B2 | 1/2003 | Swartz et al. | |
| 6,635,055 B1 | 10/2003 | Cronin | |
| 6,663,625 B1 | 12/2003 | Ormsby et al. | |
| 6,813,520 B2 | 11/2004 | Truckai et al. | |
| 6,817,999 B2 | 11/2004 | Berube et al. | |
| 6,929,642 B2 | 8/2005 | Xiao et al. | |
| 7,197,363 B2 | 3/2007 | Prakesh et al. | |
| 7,226,446 B1 | 6/2007 | Mody et al. | |
| 7,864,160 B2 | 1/2011 | Geaghan et al. | |
| 8,808,281 B2 | 8/2014 | Emmons et al. | |
| 9,615,882 B2 | 4/2017 | Shroff et al. | |
| 9,980,774 B2 | 5/2018 | Chu et al. | |
| 9,993,293 B2 | 6/2018 | Chun et al. | |
| 10,299,859 B2 | 5/2019 | Chu et al. | |
| 10,470,819 B2 | 11/2019 | Chu et al. | |
| 10,869,720 B2 | 12/2020 | Chu et al. | |
| 2003/0057413 A1 | 3/2003 | Kim et al. | |
| 2003/0109868 A1 | 6/2003 | Chin | |
| 2003/0163128 A1 | 8/2003 | Patil et al. | |
| 2003/0195499 A1 | 10/2003 | Prakash et al. | |
| 2005/0240173 A1 | 10/2005 | Palti | |
| 2006/0200119 A1 | 9/2006 | Vaska et al. | |
| 2006/0293652 A1 | 12/2006 | van Der Weide | |
| 2007/0066972 A1 | 3/2007 | Ormsby et al. | |
| 2007/0139294 A1 | 6/2007 | Dunn et al. | |
| 2007/0179552 A1 | 8/2007 | Dennis et al. | |
| 2007/0203480 A1 | 8/2007 | Mody et al. | |
| 2007/0213583 A1 | 9/2007 | Kim et al. | |
| 2008/0082093 A1 * | 4/2008 | Prakash | A61B 18/14 |
| | | | 606/33 |
| 2008/0167664 A1 | 7/2008 | Payne et al. | |
| 2009/0146439 A1 | 6/2009 | Watts | |
| 2010/0121319 A1 | 5/2010 | Chu et al. | |
| 2010/0125269 A1 | 5/2010 | Emmons et al. | |
| 2010/0137857 A1 | 6/2010 | Shroff et al. | |
| 2010/0137860 A1 | 6/2010 | Demarais et al. | |
| 2011/0004205 A1 | 1/2011 | Chu et al. | |
| 2011/0040300 A1 | 2/2011 | Brannan | |
| 2011/0257641 A1 | 10/2011 | Hastings | |
| 2012/0116486 A1 | 5/2012 | Naga et al. | |
| 2014/0290830 A1 | 10/2014 | Brannan | |
| 2018/0036080 A1 | 2/2018 | Dickhans et al. | |
| 2018/0303547 A1 | 10/2018 | Chu et al. | |
| 2018/0318005 A1 | 11/2018 | Chu et al. | |
| 2018/0344397 A1 | 12/2018 | Chu et al. | |
| 2019/0380776 A1 | 12/2019 | Chu et al. | |

FOREIGN PATENT DOCUMENTS

| | | |
|---|---|---|
| WO | WO 1997/006739 | 2/1997 |
| WO | WO 2003/053259 | 7/2003 |
| WO | WO 2003/088858 | 10/2003 |
| WO | WO 2006/004585 | 1/2006 |
| WO | WO 2009/146439 | 12/2009 |
| WO | WO 2010/048334 | 4/2010 |
| WO | WO 2010/048335 | 4/2010 |
| WO | WO 2010/053700 | 5/2010 |
| WO | WO 2012/003232 | 1/2012 |
| WO | WO 2013/149245 | 10/2013 |

* cited by examiner

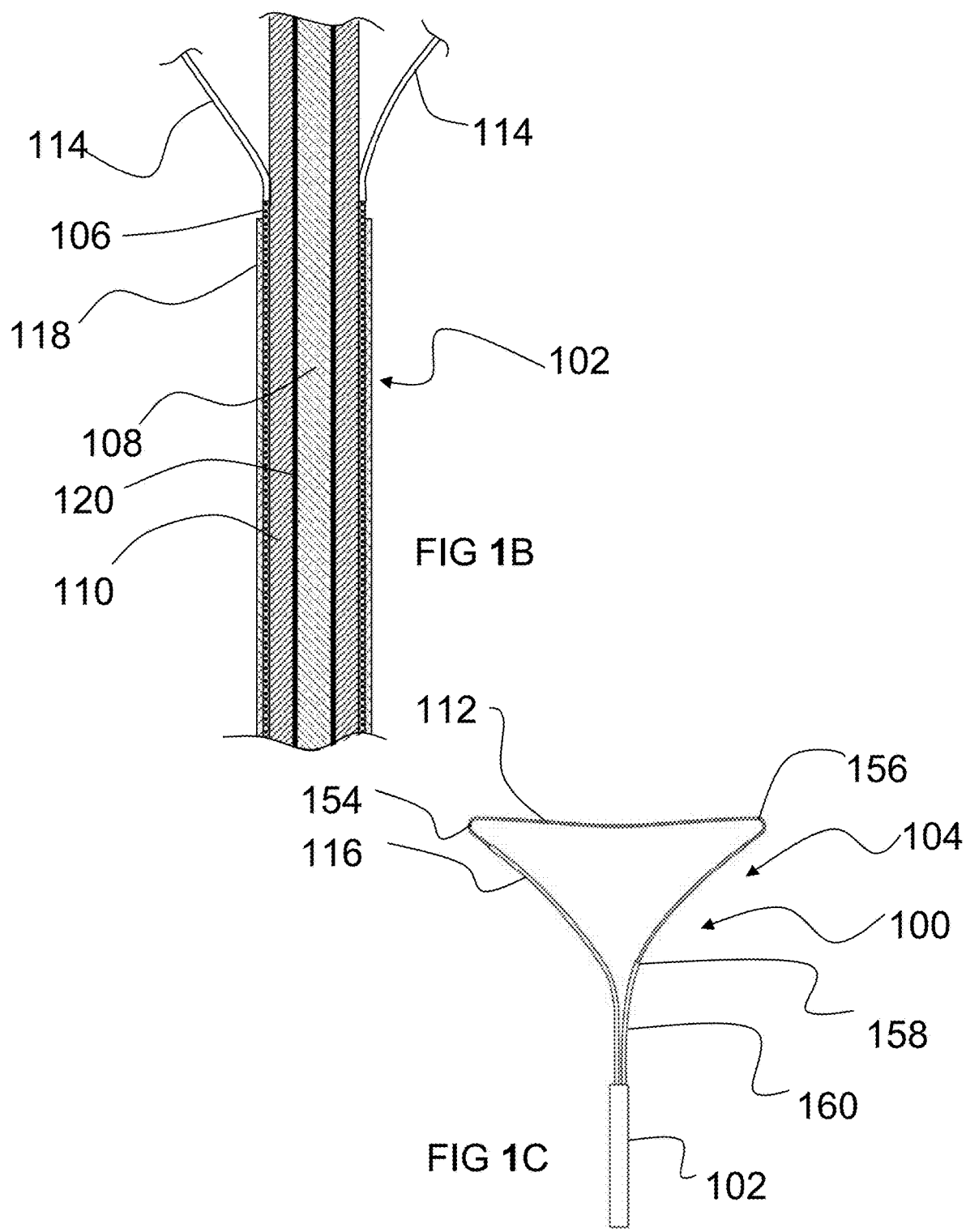

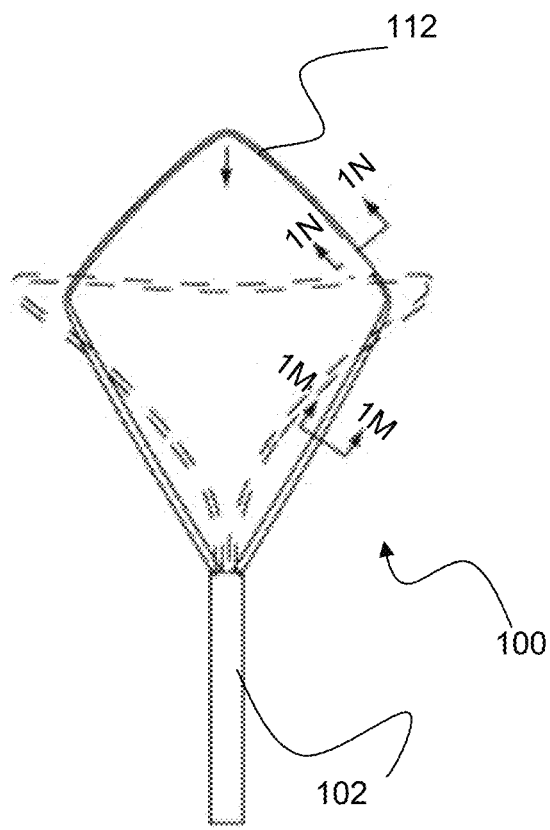
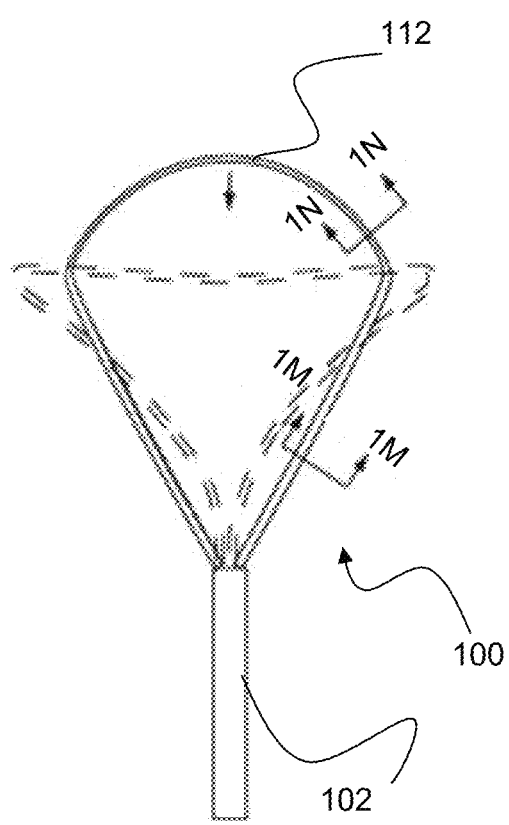
FIG 1K FIG 1L
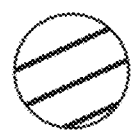
FIG 1M FIG 1N

METHODS AND DEVICES FOR APPLYING ENERGY TO BODILY TISSUES

CROSS-REFERENCE TO RELATED APPLICATIONS

This application is a continuation of Ser. No. 15/974,386 filed May 8, 2018, which is a continuation of U.S. patent application Ser. No. 12/603,349 filed Oct. 21, 2009, now U.S. Pat. No. 9,993,293 issued Jun. 12, 2018, which claims priority of U.S. Provisional Application Nos. 61/113,189, filed on Nov. 10, 2008; 61/113,192, filed on Nov. 10, 2008; 61/113,194, filed on Nov. 10, 2008; 61/162,241, filed on Mar. 20, 2009; 61/162,244, filed on Mar. 20, 2009; and 61/222,409, filed on Jul. 1, 2009. The contents of which are incorporated herein by reference in their entireties.

FIELD OF THE INVENTION

This invention relates to devices and methods for ablation of soft tissues of the body and, more specifically, to microwave ablation devices designed to generate microwave fields for therapeutic tissue ablation.

BACKGROUND OF THE INVENTION

There are several clinical conditions that can be treated by ablation. Examples of such conditions include cancer, Menorrhagia, atrial fibrillation, wrinkles, etc. Menorrhagia is one of the most common gynecological conditions in pre-menopausal women. It is characterized by excessive menstrual blood loss. Objectively, Menorrhagia is defined as blood loss of more than 80 ml per menstrual cycle. The condition severely affects the quality of life of the affected women since it may interfere with physical activity, work and sexual activity. In some cases, it leads to iron deficiency anemia. Further, there is an emerging need for an easy-to-use, low cost procedure among women who want to reduce or eliminate non-clinical menstrual bleeding for lifestyle reasons.

The usual first line of treatment is drugs such as oral contraceptive pills and synthetic Progesterone supplements. However, drugs are not effective in a significant percentage of patients.

In patients with refractory disease, the classical treatment is hysterectomy. Hysterectomy is an invasive surgery involving the surgical removal of the uterus—a major organ in the body. The surgery requires 2-4 days of hospitalization and has a 3 to 6 week recovery period. Further, it carries surgical risks due to the use of general anesthesia.

As an alternative to hysterectomy, several techniques have been developed that aim to destroy only the endometrium in a minimally invasive manner called endometrial ablation. Endometrial ablation can be performed by a variety of techniques such as radiofrequency heating, circulating hot saline in the uterine cavity, microwave heating, cryodestruction, laser destruction, etc. Endometrial ablation in general has been established as an effective therapy for the treatment of Menorrhagia. However, every current endometrial ablation technique has some fundamental limitations. For example, the Hydrothermablator™ device by Boston Scientific circulates hot saline in the uterine cavity to thermally destroy the endometrium. Uterine size and shape is rarely a limitation to performing this procedure since the saline conforms well to even an irregularly shaped endometrial surface. However, the device needs a hysteroscope which adds to the procedure cost and complexity. Further the device is thick and rigid. Because of that, the procedure requires significant anesthesia, usually in the form of conscious sedation or general anesthesia.

Currently, the market leader for endometrial ablation is Novasure™, a device that uses radiofrequency energy delivered through a triangular three dimensional metallic mesh to destroy the endometrial lining. Even though the device is the market leader, it has several fundamental disadvantages. The device shaft is thick and rigid. Thus a significant amount of cervical dilation is needed to introduce the device into the uterine cavity. Since cervical dilation is very painful, the procedure requires significant anesthesia, usually in the form of conscious sedation or general anesthesia. Further, the fairly rigid, three dimensional, triangular metallic mesh is unable to conform to irregularly-shaped uterine cavities. This reduces the total potential pool of patients that can be treated by the device. Also, the device is expensive (~$900). This limits the use of the devices not just in developing countries, but also in the US. In the US, the total reimbursement for an endometrial ablation procedure performed in the office is fixed. When the cost of the expensive device is added to the cost of the personnel and equipment required for conscious sedation, the profit margins of performing physicians shrink dramatically or even disappear totally.

Thus, even though there are a variety of endometrial ablation products, there is still a need for a small-size, flexible, low-cost, easy to use device in this large and growing market.

BRIEF SUMMARY OF THE INVENTION

The present invention discloses devices and methods for treating tissue with microwave energy. In several embodiments, microwave energy is used for ablating tissue. One application for such ablation is treating menorrhagia by endometrial ablation.

The present invention discloses methods and devices to create one or more area or volumetric lesions. The present invention discloses various embodiments of flexible, low-profile devices that can be inserted non-invasively or minimally invasively into or near the target tissue.

Some of the embodiments herein may be broadly described as microwave devices comprising a transmission line (e.g. a coaxial cable) and an antenna at the distal end of the coaxial cable. The antenna comprises a radiating element that extends from the distal end of the coaxial cable. For example, the radiating element may be a continuation of the inner conductor of the coaxial cable or may be an additional element connected to the inner conductor of the coaxial cable. The radiating element radiates a microwave field that is characteristic of its specific design. The radiated microwave field causes agitation of polarized molecules, such as water molecules, that are within target tissue. This agitation of polarized molecules generates frictional heat, which in turn raises the temperature of the target tissue. Further, the microwave field radiated by the radiating element may be shaped by one or more shaping element(s) in the antenna. The shaping element(s) may be electrically connected to the outer conductor of the coaxial cable. Several embodiments of the radiating element and the shaping element and combinations thereof are described herein. A significant portion of the disclosure discloses embodiments of ablation devices, wherein the radiating element is shaped like a loop and the shaping element is shaped like a loop. The cross section shapes of the radiating element and shaping element may be designed to achieve the desired mechanical and microwave properties. Examples of such cross section shapes include, but are not limited to round, oval, rectangular, triangular, elliptical, square, etc.

The present invention discloses several microwave antennas designed to generate a unique ablation profile that can ablate an entire large area or large volume target tissue in a single ablation. The ablation profile can be purposely shaped by designing the antenna. For example, the ablation profile may be designed to create a deeper ablation in the center of a target organ and shallower ablation towards the periphery of the target organ.

The antennas disclosed herein may be deployed before being placed in the vicinity of or inside of the target tissue. Alternately, the antennas may be deployed after being placed in the vicinity of or inside of the target tissue. The deployment of the antennas disclosed herein may be done by one of several methods. The antenna may simple be navigated to the target tissue in a full deployed configuration. For example, the antenna may be navigated to the surface of liver in a full deployed configuration through a laparotomy. The antenna may be deployed through an introducer in which the antenna is in a collapsed, low-profile configuration when inside the introducer and is deployed after the antenna exits the introducer. The antenna may be deployed after the antenna exits the introducer by one or more of: the elastic property of the antenna or its components, the superelastic property of the antenna or its components, the shape memory property of the antenna or its components, use of a mechanical deployment mechanism for the antenna or its components, use of one or more anatomical regions to change the shape of one or more antenna portions, etc. One or more portions of the antennas herein may be malleable or plastically deformable. This allows the user to shape an antenna to ensure better contact with target tissue or better navigation through the anatomy.

The devices disclosed herein comprise antennas wherein the ablation profile generated by an antenna is tailored and optimized for a particular clinical application. For example, in the embodiments wherein a microwave antenna is used to ablate the wall of a cavity such as the uterine cavity, the ablation profile may be designed to ablate substantially the entire wall of the cavity without the need for repositioning of the antenna.

The antennas disclosed herein may be conformable to acquire the shape of a portion of the target anatomy or otherwise be shaped by one or more portions of the target anatomy. For example, the antennas disclosed herein may be elastically flexible to conform to that shape of a small cavity into which the antenna is deployed. The antennas disclosed herein may be sized and shaped to approximate the size and shape of the target anatomy such as the uterine cavity.

The ablation devices disclosed herein may be designed to be slim and flexible. This allows the user to introduce such ablation devices minimally invasively through small incisions or opening or even non-invasively through natural openings or passageways. Examples of minimally invasive introduction includes percutaneous introduction through the vasculature. Examples of non-invasive introduction includes introduction from the anus, mouth or nostrils into the gastro-intestinal tract, introduction from the vagina into the female reproductive system, introduction from the urethra into the urinary system, introduction from the ear, nostrils or mouth into the ENT system, etc. The devices and methods disclosed herein may be used to ablate diseased tissue or healthy tissue or unwanted tissue in organs or artificially created cavities. The devices disclosed herein may be introduced through laparoscopic, thoracoscopic, cystoscopic, hysteroscopic or other endoscopic openings or instrumentation into or near organs or bodily cavities. The methods disclosed herein may be performed under real-time monitoring e.g. by direct visual observation, hysteroscopy, cystoscopy, endoscopy, laparoscopy, ultrasound imaging, radiologic imaging, etc.

Various additional features may be added to the devices disclosed herein to confer additional properties to the devices disclosed herein. Examples of such features include, but are not limited to one or more lumens, ability to apply a vacuum or suction to the target anatomy, ability to visualize one or more regions of the target anatomy, ability to limit the depth of insertion into the target anatomy, ability to deploy the antenna, ability to connect to a source of energy, etc.

Several of the method and device embodiments are designed to minimize the use of anesthesia such that the methods may potentially be performed using only local anesthesia.

The dimensions or other working parameters of the devices disclosed herein may be adjustable or programmable based on user inputs. The user input may be based on factors such as patient's anatomical data including anatomical dimensions and the desired level of safety and efficacy.

In one variation, the present disclosure includes a medical device for applying microwave energy to a surface within a tissue cavity. For example, the device can include a transmission line; a flexible antenna electrically coupled to the transmission line and moveable between a first undeployed configuration and a second deployed configuration, the antenna comprising an elongate first conductor arranged in a first planar profile when in the deployed configuration, wherein in the deployed configuration the antenna is configured to generate a volumetric microwave field upon application of the microwave energy, where the first planar profile of the first conductor is selected based upon the tissue cavity to produce the microwave field sized to the tissue cavity antenna such the microwave field applies energy to substantially an entire surface of the tissue cavity in a single activation without repositioning.

In an additional variations, the antenna as described herein can further comprise a second conductor electrically coupled to a shielding element of the transmission line, where the second conductor comprises a second planar profile configured such that upon the application of microwave energy to the first conductor, the second conductor alters output of the first conductor to produce the volumetric microwave field.

The first planar profile can be shaped to generate the volumetric microwave field to apply energy to a uterine cavity. Moreover, a deployed configuration of the antenna can substantially approximate the shape of the uterine (or other) cavity. In any case, such cavity ablating device will employ an antenna that can generate a volumetric microwave field to ablate the entire cavity in a selective manner. In one example, when the antenna is used in a uterine endometrium, the antennae can be configured such that a lesion on the endometrium is deeper in the center of the uterine cavity and is shallower at a cornual region and shallower at a lower uterine region.

The present disclosure also includes methods of delivering energy to a surface of a cavity in tissue. These methods can include inserting a microwave ablation device into the cavity, the microwave ablation device comprising a transmission line and a microwave antenna, where the microwave antenna comprises a first planar conductor and a planar shaping element; applying energy to microwave ablation device, where during the application of energy, the planar shaping element alters the energy output of the planar conductor to produce a volumetric microwave field to deliver energy to substantially an entire surface of the cavity.

As described herein, one benefit of shaping the volumetric microwave field to match the cavity allows for minimum treatment cycles or even a single treatment cycle. Accordingly, the method can include applying energy to generate the volumetric microwave field in the cavity to provide a therapeutically effective amount of energy to the cavity without repositioning the microwave antenna.

The method can also include the use of an introducer or sheath device where the microwave antenna deploys through the sheath and into the cavity. The use of the sheath or introducer allows for cooling or suction to be performed in the cavity. In alternative variations, the cooling or suction can take place through a shaft of the device thereby eliminating the need for a separate introducer or sheath.

The antennas disclosed herein may use unique properties of microwaves such as the interaction of microwaves with additional shaping elements (e.g. metallic objects) in the antenna to shape the microwave field. For example, additional shaping elements in the antenna may be used to create a more distributed microwave field. The shaping elements in the antenna may also be used to improve the power deposition by the antenna. The additional elements in the antenna are not in direct electrical conduction with the inner conductor of the coaxial feed cable. In several of the embodiments disclosed herein, a conductive shaping element (e.g. a loop shaped element) connected to the outer conductor of a coaxial feed line is used to shape the microwave field.

BRIEF DESCRIPTION OF THE SEVERAL VIEWS OF THE DRAWINGS

FIG. 1B shows a section of ablation device 100 of FIG. 1A through a coaxial cable.

FIG. 1C shows a view of an antenna similar to the antenna of FIG. 1A without a center loop.

FIGS. 1K and 1L show two alternate embodiments of shapes of microwave antennas of ablation devices.

FIG. 1M shows the substantially circular cross-section of the microwave antenna of FIGS. 1K and 1L through plane 1M-1M.

FIG. 1N shows two alternate cross-sections of microwave antenna of FIGS. 1K and 1L through plane 1N-1N.

DETAILED DESCRIPTION OF THE INVENTION

Figure 1A:
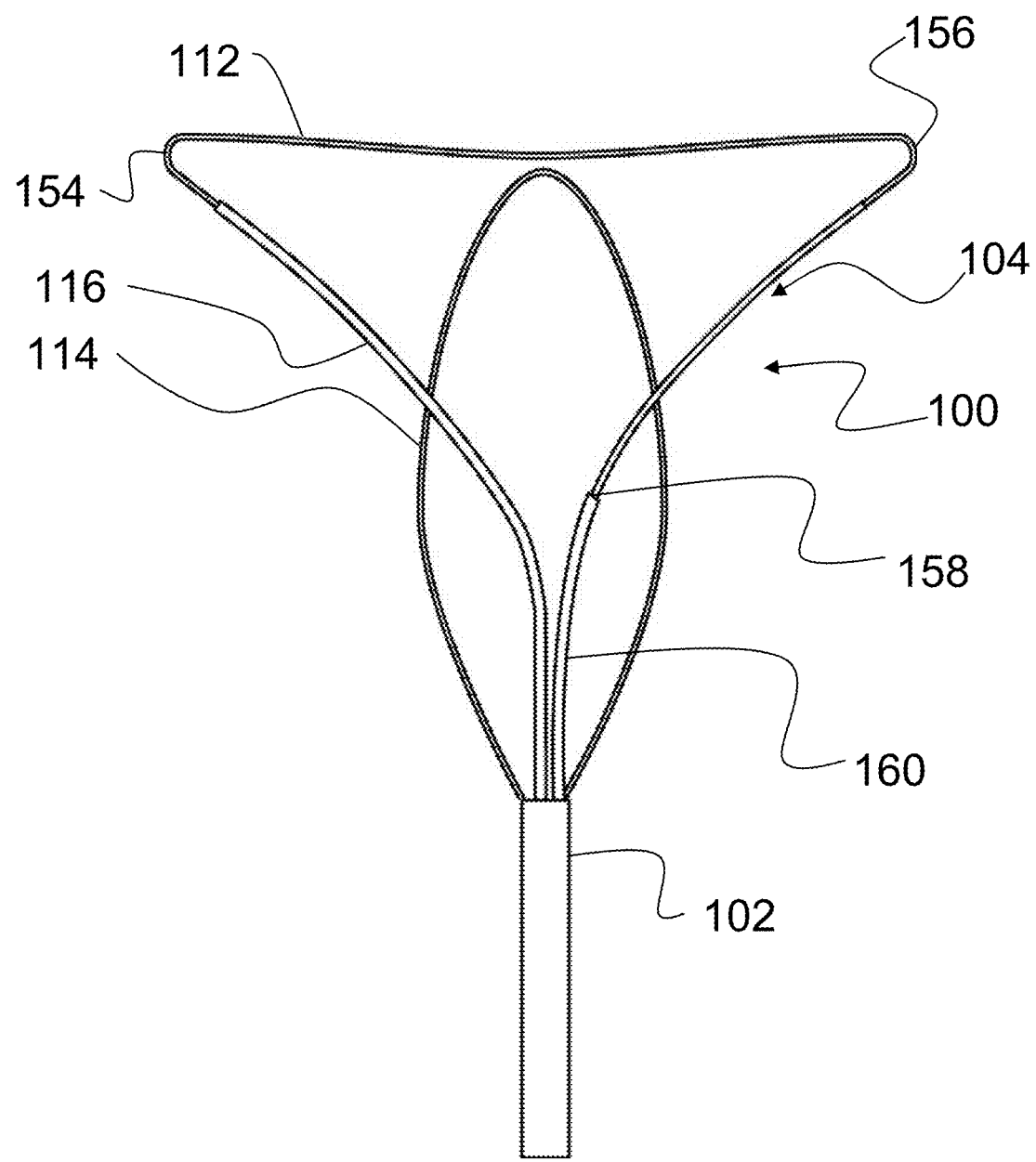
FIG. 1A shows a view of an antenna of a microwave ablation device optimized for endometrial ablation.

This specification discloses multiple systems, structures and devices, and associated methods, which employ various aspects of the invention. While these systems, structures and devices, and associated methods, are discussed primarily in terms of microwave based ablation systems used for ablating uterine endometrium, it should be appreciated that methods and devices disclosed herein are applicable for use in other bodily structures, as well. For example, the various aspects of the invention can be used for ablating tissue in, or adjacent to, the brain, prostate and other portions of the male urinary tract, gall bladder, uterus and other portions of the female reproductive tract, regions of the vasculature, intestine and other portions of the lower alimentary tract, stomach and other portions of the upper alimentary tract, liver and other digestive organs, lungs, skin, mucus membranes, kidneys, reproductive organs, or other organs or soft tissues of the body.

Several devices and methods disclosed herein are used to treat menorrhagia by microwave thermal ablation. Microwave thermal ablation does not depend on the conduction of electricity to tissue unlike RF ablation. Thus, devices using microwave thermal ablation such as the devices disclosed herein don't need good contact with tissue. They can function well even without perfect contact with the target tissue. Thus, the devices disclosed herein do not require extremely precise placement in tissue, thereby reducing the dependence of procedure outcome on physician skills. The devices herein are designed to have a distal microwave emitting antenna and a proximal shaft. The proximal shaft comprises a flexible coaxial cable that delivers microwave energy from a microwave generator to the microwave emitting portion. The shaft is slim (e.g. <3 mm) and flexible so that minimal forces are exerted on the cervix during the procedure. The flexible nature of the shaft enables the shaft to take the natural shape of passage during introduction instead of distorting the natural shape of the passage by the shaft of the device. For example, when a device is introduced transcervically into the uterus, the shaft may acquire the shape of introduction passage comprising the vagina, cervical canal and uterine cavity instead of distorting one or more of the vagina, cervical canal and uterine cavity. The device shaft may be designed to be capable of bending by more than 45 degrees when it experiences distorting forces by the anatomy. Further, the slim and flexible nature of the devices herein enables the procedure to be performed without cervical dilation. Cervical dilation if needed is minimal. This dramatically reduces the discomfort to the patient consequently significantly reducing the requirement of anesthesia. This has tremendous clinical advantages since now the procedure can be performed in the physician's office under local anesthesia.

All the experiments herein were performed at 0.915 GHz ISM band. Antennas, methods, etc. disclosed herein may be used with or without modifications at other frequencies including, but not limited to ISM bands of 0.433 GHz, 2.45 GHz, 5.8 GHz, etc. The microwave power generator may be magnetron based or solid state. The microwave power generator may be single or multi-channel. The microwave power generator used for the experiments comprised a Vector Network Analyzer (Agilent 8753 series) and amplifier modules build in-house using transistors from Freescale Semiconductor (Austin, Tex.). The power measurement was made using a power meter (ML2438A Power Meter, Anritsu Company, Richardson, Tex.). Similar devices and components can be used to design the microwave generator for clinical use with the devices and methods disclosed herein.

In the experiments, where desired, a fiber optic thermometry system (FOT Lab Kit by LumaSense Technologies, Santa Clara, Calif.) was used to measure the temperature at several locations in the tissue. The fiber optic thermometry system was used since it has no metallic components that can interfere with the microwave field. Similar non-interfering thermometry may be used to measure the temperature at one or more locations during an ablation procedure.

Several embodiments of planar antennas 104 are also included in variations of the devices described herein. Such planar antennas 104 may be used to ablate or otherwise treat planar or non-planar tissue regions. Such planar antennas 104 may comprise single or multiple splines, curves or loops in a generally planar arrangement. Planar antennas 104 may be used for ablating a surface such as the surface of organs such as liver, stomach, esophagus, etc. In a one embodiment, a single microwave signal is fed to an antenna 104 through a transmission line. Antenna 104 generates a microwave field. The near field portion of the microwave field generated by antenna 104 may be used for tissue ablation. For example, FIG. 1A shows a view of a planar antenna of a microwave ablation device designed for endometrial ablation. In FIG. 1A, microwave ablation device 100 comprises a transmission line (such as a coaxial cable 102) terminating in an antenna 104 at the distal end of the transmission line. In one embodiment, a single microwave signal is fed to antenna 104 through coaxial cable 102. The shape of antenna 104 is substantially triangular and has a wider distal region and a narrower proximal region. This shape is similar to the shape of the uterine cavity and thus conforms to the shape of the uterine cavity. Antenna 104 generates a microwave field. The near field of the microwave field generated by antenna 104 is used for endometrial ablation. In FIG. 1A, antenna 104 comprises a radiating element in the form of an outer loop 112 and a shaping element in the form of a bent or curved metallic center loop 114. Outer loop 112 and center loop 114 may physically touch each other when deployed in the anatomy. In one embodiment, outer loop 112 is a continuation of the inner conductor of coaxial cable 102. Center loop 114 shapes or redistributes the microwave field radiated by outer loop 112. It should be noted that there is no direct electrical conduction between outer loop 112 and center loop 114. When microwave energy is delivered through coaxial cable 102 to antenna 104, a first microwave field is emitted by outer loop 112. The first microwave field interacts with center loop 114. This interaction induces a leakage current on center loop 114. The leakage current in turn creates a second microwave field. The first microwave field and the second microwave field together combine to produce a unique shaped microwave field of antenna 104 that is clinically more useful that the unshaped microwave field generated by an antenna 104 comprising only outer loop 112. Thus the original microwave field is redistributed by the design of center loop 114. Center loop 114 alone is not capable of functioning as an antenna; rather center loop 114 shapes or redistributes the electromagnetic or microwave field emitted by outer loop 112 to produce a shaped microwave field that is clinically more useful. Further, the combination of outer loop 112 and center loop 114 improves the power deposition of antenna 104.

It should be noted that there is no direct electrical conduction between outer loop 112 and center loop 114. Antenna 104 further comprises one or more antenna dielectrics 116 covering one or more portions of one or both of: outer loop 112 and s center loop 114. In FIG. 1A, an antenna dielectric 116 covers the proximal portion of outer loop 112. Any of the antenna dielectrics 116 disclosed herein may be used to shape the microwave field and to optimize the performance of antenna 104. Any of the antenna dielectrics 116 disclosed herein may be one or more conducting polymers.

Figures 1D, 1E:
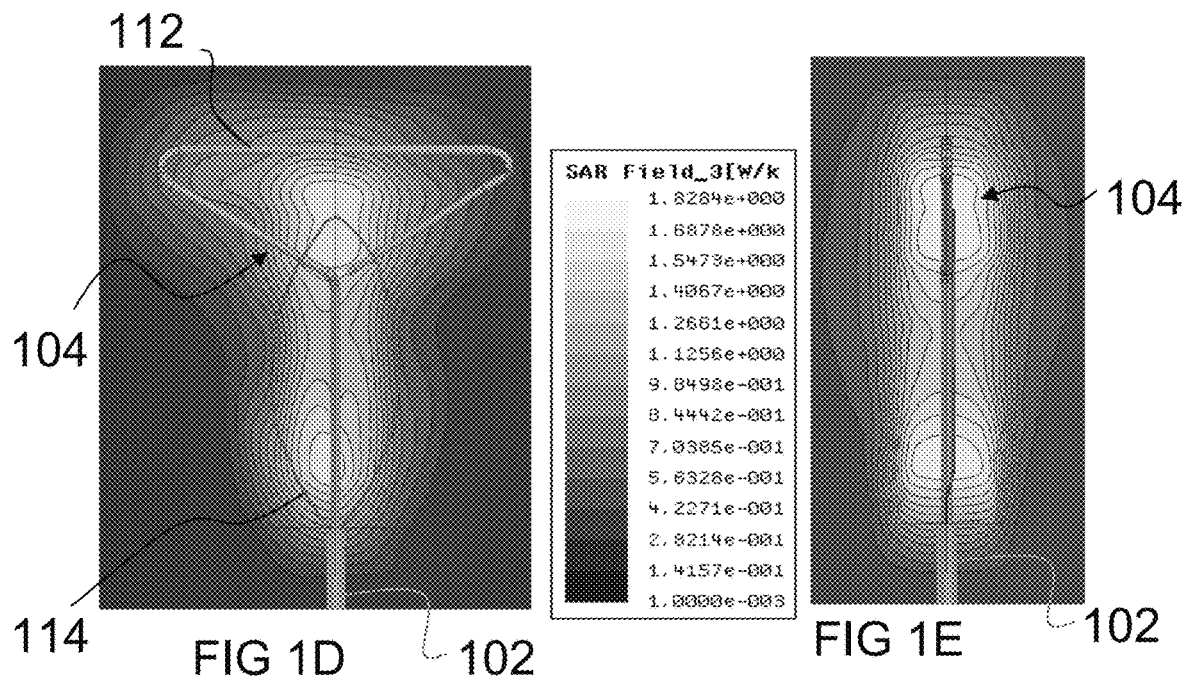
FIGS. 1D and 1E show the front and side views respectively of the SAR profile generated by an antenna with a center loop similar to the antenna of FIG. 1A.

A microwave field couples to the nearest conductive path. In several embodiments of antenna 104 disclosed herein, the nearest conductive path is provided by center loop 114. Thus the microwave field couples to center loop 114 instead of coupling to the shielding element of the transmission line (e.g. the outer conductor 106 of the feeding coaxial cable 102). Therefore, minimal microwave field is coupled proximally to the shielding element of the transmission line. This in turn creates a unique, shaped or redistributed microwave field that does not significantly extend proximally to antenna 104 as shown in FIGS. 1D and 1I.

In one embodiment, outer loop 112 has no sharp corners. Sharp corners in outer loop 112 may cause the field to concentrate in the vicinity of the sharp corners. In one embodiment, the minimal radius of curvature of a corner in outer loop 112 is at least 0.5 mm. In the embodiment in FIG. 1A, the radius of curvature of corner regions 154 and 156 in outer loop 112 is about 1 mm+/−0.3 mm.

In one embodiment, antenna 104 has a shape that substantially approximates the shape of the body organ to be ablated. For example, antennas in FIGS. 1A, 1D and 1I have a roughly triangular, planar shape that approximates the roughly triangular, planar shape of the uterine cavity and is especially suited for endometrial ablation. The antennas 104 may be positioned such that the plane of the antenna is parallel to the plane of the uterine cavity. The proximal portion of the antenna 104 is directed towards the cervix and corner regions 154 and 156 of outer loop 112 are directed towards the fallopian tubes. However, as mentioned before, microwave thermal ablation does not necessarily require perfect contact with all of the target tissue. Thus antenna 104 is able to ablate all or substantially all of the endometrium. The entire endometrium can be ablated in a single ablation by antenna 104 having a single microwave antenna. Thus, repositioning of antenna 104 after an ablation is not needed. This greatly reduces the amount of physician skill needed for the procedure. Further, multiple antennas 104 are not needed in ablation device 100. A single antenna 104 positioned at a single location is able to ablate a therapeutically sufficient amount of the endometrium. This simplifies the design of ablation device 100.

Further, antenna 104 in the working, deployed configuration is generally flat and sufficiently flexible such that during and after introduction and deployment of antenna 104 in the anatomy, the anatomy experiences only slight forces from antenna 104. This may be achieved by designing an antenna 104 comprising one or more flexible outer loop 112, one or more flexible center loop 114 and one or more flexible antenna dielectrics 116. The plane of outer loop 112 is substantially parallel to the plane of center loop 114. Thus, the uterine walls experience only slight forces from antenna 104. This in turn reduces or eliminates the distension of the uterine wall thereby reducing the discomfort to the patient. This in turn further reduces the anesthesia requirements. Flexible antenna 104 may easily be introduced in a collapsed, undeployed configuration through a small lumen thereby eliminating or minimizing any cervical dilation. In such a collapsed, undeployed configuration, both outer loop 112 and center loop 114 are in a small profile, linearized configuration. The lack of cervical dilation dramatically reduces the discomfort to the patient consequently significantly reducing the requirement of anesthesia. This has tremendous clinical advantages since now the procedure can be performed in the physician's office under local anesthesia. In the collapsed configuration, outer loop 112 and center loop 114 may be closer to each other than in the non-collapsed configuration. This enables the introduction of antenna 104 through narrow catheters, shafts, introducers and other introducing devices. Further, this enables the introduction of antenna 104 through small natural or artificially created openings in the body.

Further, flat and flexible antenna 104 in FIG. 1A in its deployed configuration has an atraumatic distal end in which the distal region of antenna 104 is wider than the proximal portion of antenna 104. This design creates an atraumatic antenna 104 which in turn reduces the risk of perforation of the uterus. The flexible nature of antenna enables antenna 104 to take the natural shape of passage during introduction instead of distorting the passage. For example, when antenna 104 is introduced trans-cervically into the uterus, antenna 104 may acquire the shape of introduction passage comprising the vagina, cervical canal and uterine cavity instead of distorting one or more of the vagina, cervical canal and uterine cavity.

In one embodiment, the length of outer loop 112 measured along the outer loop 112 from the distal end of coaxial cable 102 or other transmission line until the distal end of outer loop 112 is an odd multiple of one quarter of the effective wavelength at one of: 433 MHz ISM band, 915 MHz ISM band, 2.45 GHz ISM band and 5.8 GHz ISM band. In one embodiment of a deployed configuration of antenna 104 as shown in FIG. 1A, the length of outer loop 112 measured along the outer loop 112 from the distal end of coaxial cable 102 until the distal end 158 of outer loop 112 is about three quarters of the effective wavelength at the 915 MHz ISM band. The effective wavelength is dependent on the medium surrounding the antenna and the design of an antenna dielectric on the outer loop 112. The design of the antenna dielectric includes features such as the type of dielectric(s) and thickness of the dielectric layer(s). The exact length of the outer loop 112 is determined after tuning the length of outer loop 112 to get good impedance matching. The length of the outer loop 112 in one embodiment is 100+/−15 mm. In one embodiment, the width of deployed outer loop 112 is 40+/−15 mm and the longitudinal length of deployed outer loop 112 measured along the axis of coaxial cable 102 is 35+/−10 mm. In the embodiment shown in FIG. 1A, distal end 158 of outer loop 112 is mechanically connected to the distal end of coaxial cable 102 by an elongate dielectric piece 160.

In one embodiment, the proximal portion of outer loop 112 is designed to be stiffer and have greater mechanical strength than the distal portion. In the embodiment shown in FIG. 1A, this may be achieved by leaving original dielectric material 110 of coaxial cable 102 on the proximal portion of outer loop 112. In an alternate embodiment, this is achieved by coating the proximal portion of outer loop 112 by a layer of antenna dielectric.

In the embodiment shown in FIG. 1A, the cross sectional shape of outer loop 112 may or may not be uniform along the entire length of outer loop 112. In this embodiment, the proximal portion of outer loop 112 is a continuation of the inner conductor of coaxial cable 102. This portion has a substantially circular cross section. A middle portion of outer loop 112 has a substantially flattened or oval or rectangular cross section. The middle portion may be oriented generally perpendicular to the distal region of coaxial cable 102 in the deployed configuration. The middle portion of outer loop 112 is mechanically designed to bend in a plane and comprise one or more bends after deployment in the anatomy. This in turn ensures that the distal most region of ablation device 100 is atraumatic and flexible enough to conform to the target tissue anatomy. This helps in the proper deployment of outer loop 112 in the uterus. In one embodiment, the middle portion of outer loop 112 is a continuation of inner conductor of coaxial cable 102 and is flattened. In one embodiment, the distal most portion of outer loop 112 is a continuation of inner conductor of coaxial cable 102 and is non-flattened such that it has a circular cross section.

One or more outer surfaces of outer loop 112 may be covered with one or more layers of antenna dielectrics 116. One or more outer surfaces of center loop 114 may be covered with one or more layers of antenna dielectrics 116. The thickness and type of antenna dielectric material along the length of outer loop 112 is engineered to optimize the microwave field shape. In one embodiment shown in FIG. 1A, every portion of outer loop 112 is covered with some antenna dielectric material such that no metallic surface of outer loop 112 is exposed to tissue. Thus, in the embodiment of FIG. 1A, outer loop 112 is able to transmit a microwave field into tissue, but unable to conduct electricity to tissue. Thus, outer loop 112 is electrically insulated from surrounding tissue. Thus, in the embodiment of FIG. 1A, there is no electrical conduction and no conductive path between outer loop 112 and center loop 114 even though outer loop 112 and center loop 114 may physically touch each other when deployed in the anatomy. Examples of dielectric materials that can be used as antenna dielectrics in one or more embodiments disclosed herein include, but are not limited to EPTFE, PTFE, FEP and other floropolymers, Silicone, Air, PEEK, polyimides, cyanoacrylates, epoxy, natural or artificial rubbers and combinations thereof. In the embodiment of FIG. 1A, the antenna dielectric 116 on the proximal portion of outer loop 112 is a continuation of the dielectric 110 of coaxial cable 102. There may be an additional layer of a stiffer antenna dielectric 116 over this later of antenna dielectric 116. In the embodiment of FIG. 1A, the dielectric on the middle portion of outer loop 112 is a silicone layer with or without impregnated air or a silicone tube enclosing a layer of air. In the embodiment of FIG. 1A, the dielectric on the distal most portion of outer loop 112 is a silicone layer with or without impregnated air or a silicone tube enclosing a layer of air or EPTFE. The thickness of an antenna dielectric on any portion of outer loop 112 may vary along the length of outer loop 112. Further, the crossection of an antenna dielectric on any portion of outer loop 112 may not be symmetric. The various configurations of the antenna dielectric are designed to achieve the desired ablation profile as well as achieve the desired impedance matching or power efficiency. In an alternate embodiment, entire outer loop 112 is covered with silicone dielectric. In one such embodiment, the layer of silicone used to coat the distal most portion of outer loop 112 may be thinner than the layer of silicone used to coat the middle portion of outer loop 112. The thinner silicone dielectric compensates for the lower field strength that normally exists at the distal most portion of a radiating element such as outer loop in FIG. 1A. Thus, the microwave field is made more uniform along the length of outer loop 112. In one device embodiment, outer loop 112 is made of a metallic material and the circumference of the metallic material of the distal region of outer loop 112 is more than the circumference of the metallic material of the middle portion of outer loop 112. This causes the silicone dielectric to stretch more at the distal portion than at the middle portion of outer loop 112. This in turn generates a thinner layer of antenna dielectric at the distal portion of outer loop 112 than at the middle portion of outer loop 112. In another embodiment, entire outer loop 112 is made from a single length of metallic wire of a uniform crossection. In this embodiment, a tubular piece of silicone dielectric of varying thickness is used to cover outer loop 112. The tubular silicone dielectric is used to cover the distal and middle portions of outer loop 112 such that the layer of silicone dielectric is thinner near the distal portion and thicker near the middle portion of outer loop 112.

In FIG. 1A, the shape of outer loop 112 is different from the shape of center loop 114. Further, in FIG. 1A, outer loop 112 and center loop 114 are both substantially planar and the plane of outer loop 112 is substantially parallel to the plane of center loop 114. Further, in FIG. 1A, both outer loop 112 and center loop 114 are bent or non-linear.

FIG. 1B shows a section of ablation device 100 of FIG. 1A through the distal end of a coaxial cable 102. Coaxial cable 102 used herein is flexible and comprises an inner conductor 108 made of Nitinol with a Ni content of 56%+/−5%. The outer diameter of inner conductor 108 is 0.0172"+/−0.004". Inner conductor 108 has a cladding or plating 120 of a highly conductive metal such as Ag or Au. In one embodiment, inner conductor 108 comprises a silver cladding 120 of thickness 0.000250"+/−0.000050". Cladding 120 in turn is surrounded by dielectric material 110. In one embodiment, dielectric material 110 is made of expanded PTFE with an outer diameter of 0.046"+/−0.005". The dielectric material 110 in turn is surrounded by the outer conductor 106. Outer conductor 106 acts as a shielding element to the microwave signals transmitted by inner conductor 108. Further, outer conductor 106 shields the microwave signals transmitted by inner conductor 108 from external noise. In one embodiment, outer conductor 106 comprises multiple strands of Ag plated Cu. The multiple strands of outer conductor 106 are arranged such that the outer diameter of outer conductor 106 is 0.057"+/−0.005". Outer conductor 106 in turn is covered by an outer jacket 118. In one embodiment, outer jacket 118 is made of PTFE with an outer diameter of 0.065"+/−0.005". Thus, the outer diameter of coaxial cable 102 is less than about 2 mm. Similar embodiment of coaxial cable 102 may be designed that are flexible and have a diameter of less than 4 mm. Further, coaxial cable 102 is sufficiently flexible such that it conforms to a curved introduction passage comprising the vagina and the cervical canal during insertion of antenna 104 into the uterine cavity. The low profile and flexibility of the coaxial cable 102 has tremendous clinical advantages since it requires minimal or no cervical dilation during transcervical insertion. Coaxial cable 102 may be stiffened or strengthened if desired by adding one or more stiffening or strengthening elements such as jackets, braids or layers over coaxial cable 102. In FIG. 1B, the identity of coaxial cable 102 ends at the distal end of outer conductor 106. The outer jacket 118 ends a small distance proximal to the distal end of outer conductor 106. Inner conductor 108, cladding 120 and dielectric material 110 extend distally from the distal end of outer conductor 106 into antenna 104. Thus, the radiating element or outer loop 112 is electrically connected to inner conductor 108. Two proximal ends of center loop 114 are electrically connected to two regions on the outer conductor 106. In one embodiment, the two proximal ends of center loop 114 are electrically connected to diametrically opposite regions on the distal end of outer conductor 106. In one embodiment, the two proximal ends of center loop 114 are soldered to the distal end of outer conductor 106. In another embodiment, the two proximal ends of center loop 114 are laser welded to the distal end of outer conductor 106. The two proximal ends of center loop 114 may be connected to the distal end of outer conductor 106 in various configurations including, but not limited to lap joint and butt joint. In an alternate embodiment, at least one of the two proximal ends of center loop 114 is not connected to the distal end of outer conductor 106. For example, at least one of the two proximal ends of center loop 114 may be electrically connected to a region of outer conductor 106 that is proximal to the distal end of outer conductor 106.

In a method embodiment, when ablation device 100 is used for endometrial ablation, antenna 104 of FIG. 1A generates a substantially uniform microwave field that is more concentrated in the center of the uterus and is less concentrated towards the cornual regions and towards the cervix or the lower uterine region. Thus, the depth of ablation generated by antenna 104 is deeper in the center of the uterus and is less deep towards the cornual regions and towards the cervix. Such a profile is clinically desired for improved safety and efficacy. In one embodiment, the ablation profile is shaped to ablate a majority of the basalis layer of the uterine endometrium. The shape of the microwave field in any of the embodiments herein may be substantially similar to the shape of the uterine endometrium. In one embodiment, center loop 114 is made of a round or flat wire. Examples of flat wires that can be used to make center loop 114 are flat wires made of Ag or Au plated Nitinol or stainless steel with a cross sectional profile of about 0.025"× about 0.007". Such a loop shaped shaping element does not act as a shield for the microwave field. This non-shielding action is visible in the SAR pattern in FIG. 1D. In FIG. 1D, there is no sharp drop in the microwave field intensity past center loop 114. In the embodiment of FIG. 1A, center loop 114 is roughly oval in shape. Two proximal ends of center loop 114 are electrically attached to two circumferentially opposite regions of the outer conductor of coaxial cable 102. In the embodiment of FIG. 1A, the width of center loop 114 is 13+/−5 mm and the length of center loop 114 is 33+/−8 mm. When ablation device 100 is used for endometrial ablation, outer loop 112 and center loop 114 both contact the endometrial tissue surface.

Center loop 114 may be mechanically independent from outer loop 112 or may be mechanically attached to outer loop 112. In the embodiment shown in FIG. 1A, center loop 114 is mechanically independent from outer loop 112 and lies on one side of outer loop 112. In an alternate embodiment, a portion of center loop 114 passes through the interior of outer loop 112. In an alternate embodiment, a portion of center loop 114 is mechanically connected to outer loop 112. This may be done for example, by using an adhesive to connect a portion of center loop 114 to outer loop 112. In an alternate embodiment, one or more portions of center loop 114 are mechanically connected to one or more portions of outer loop 112 by one or more flexible attachments.

Parts of center loop 114 may or may not be covered by one or more layers of antenna dielectric materials 116. In the embodiment of FIG. 1A, one or more or all metallic surfaces of center loop 114 are exposed to the device environment.

Portions of outer loop 112 and center loop 114 may be made from one or more of lengths of metals such as copper, Nitinol, aluminum, silver or any other conductive metals or alloys. One or more portions of outer loop 112 and center loop 114 may also be made from a metallized fabric or plastics.

FIGS. 1D and 1E show the front and side views respectively of the SAR profile generated by an antenna with a center loop similar to the antenna of FIG. 1A. In the embodiment in FIG. 1D, the distal end of outer loop 112 is mechanically and non-conductively attached to a region of outer loop 112 proximal to the distal end of outer loop 112. Thus, outer loop 112 has a substantially linear proximal region and a looped distal region. In one embodiment, the looped distal region may be substantially triangular in shape as shown in FIG. 1D. Outer diameter of antenna dielectric 116 on the proximal region of outer loop 112 may be larger than or substantially the same as the outer diameter of antenna dielectric 116 on the looped distal region of outer loop 112. Antenna dielectric 116 on the looped distal region of outer loop 112 may be a layer of silicone of varying thickness. Outer loop 112 may be made of a silver or gold clad metal such as Nitinol. Center loop 114 may be made of a silver or gold clad metal such as Nitinol. In the embodiment shown in FIGS. 1D and 1E, center loop 114 is not covered with any antenna dielectric 116. Thus the metallic surface of center loop 114 may be exposed to the surrounding. Outer loop 112 and center loop 114 may physically touch each other when deployed in the anatomy as shown in FIG. 1E. In FIG. 1D, the microwave field is shaped such that the ablation at the center of antenna 104 will be deeper than the ablation at the corners of antenna 104. This is clinically desirable for endometrial ablation. Also, FIGS. 1D and 1E show that the microwave field volumetrically envelops entire antenna 104. Also, FIGS. 1D and 1E show that the microwave field is substantially bilaterally symmetric. FIG. 1G shows the front view of the SAR profile generated by antenna 104 of FIG. 1D without center loop 114. The microwave effect of shaping element 114 in FIG. 1D can be seen by comparing FIG. 1D to FIG. 1G. FIG. 1G shows a first unshaped field that is not shaped by shaping element 114. When the antenna 104 comprises a shaping element 114 as shown in FIG. 1D, the antenna generates a shaped microwave field as shown in FIG. 1D. It should be noted that in FIGS. 1D and 1E, the shaped microwave field is more uniformly distributed over a wider area of the endometrium than in FIG. 1G. In FIG. 1G, the unshaped microwave field is more concentrated at the distal end of coaxial cable 102. A more uniformly distributed, shaped microwave field such as in FIGS. 1D and 1E is clinically desirable for endometrial ablation. Further when antenna 104 of FIG. 1D is used for endometrial ablation, the microwave field is distributed over a wider area of the endometrium that the microwave field generated by antenna 104 of FIG. 1G. This can be seen by comparing the SAR profile distal to the distal end of coaxial cable 102 in FIGS. 1D and 1E to the SAR profile distal to the distal end of coaxial cable 102 in FIG. 1G. Further, in FIG. 1G, a portion of the unshaped microwave field extends to a significant distance proximal to the distal end of coaxial cable 102. In FIGS. 1D and 1E, an insignificant portion of the microwave field extends proximally to the distal end of coaxial cable 102. Thus the microwave field profile of FIGS. 1D and 1E is advantageous over the microwave field profile of FIG. 1G since it limits collateral damage to healthy tissue. Thus the presence of center loop 114 shapes the microwave field such that the microwave field is more distributed. In absence of center loop 114, the microwave field interacts with an element of transmission line 102 such as the outer conductor of a coaxial cable. This results in a non-desirable profile of the microwave field e.g. a concentrated field around the distal end of the transmission line 102 as shown in FIG. 1G. This interaction can also cause backward heating of coaxial cable 102 that may lead to collateral damage of healthy tissue. Further, the combination of outer loop 112 and center loop 114 creates a more robust antenna 104 wherein the performance of antenna 104 is less affected by distortions during clinical use. Also, FIGS. 1D and 1E show that the microwave field volumetrically envelops entire antenna 104.

Further, the SAR profile of FIG. 1D demonstrates that the entire uterine endometrium can be ablated in a single ablation. Thus the physician can position antenna 104 at a first position and ablate substantially the entire uterine endometrium or a therapeutically sufficient amount of endometrium to treat menorrhagia. Thus the physician does not need to reposition antenna 104 after a first endometrial ablation. In one embodiment, a majority of endometrium is ablated. This novel aspect of the device and procedure greatly reduces the amount of time needed for the procedure and also reduces the procedure risks and physician skill requirements. In the embodiments disclosed herein, a combination of direct microwave dielectric heating and thermal conduction through tissue is used to achieve the desired therapeutic effect. The thermal conduction evens out any minor variations in the microwave field and enables the creation of a smooth, uniform ablation. Further, the SAR profile of FIGS. 1D and 1E demonstrates that antenna 104 is capable of ablating an entire volume surrounding antenna 104 not just ablating between the surfaces of outer loop 112 and center loop 114. Further, the SAR profile of FIGS. 1D and 1E demonstrates that antenna 104 is capable of ablating a tissue region without leaving any "gaps" of unablated tissue within that tissue region. Further, the SAR profile of FIGS. 1D and 1E demonstrates that the entire microwave field generated by antenna 104 is used for ablation. The entire microwave field comprises the microwave field around outer loop 112, the microwave field around center loop 114, the microwave field between outer loop 112 and center loop 114 and the field within center loop 114. Further, the SAR profile of FIGS. 1D and 1E demonstrates that the microwave field is located all around outer loop 112 and is not shielded or reflected by center loop 114. Thus center loop 114 does not act as a shield or reflector in the embodiment shown in FIGS. 1D and 1E.

Various embodiments of antenna 104 may be designed to generate a variety of shapes of SAR and/or the ablation profile. For example, antennas 104 may be designed to generate substantially square, triangular, pentagonal, rectangular, round or part round (e.g. half round, quarter round, etc.), spindle-shaped or oval SARs or ablation patterns.

Figure 1F:
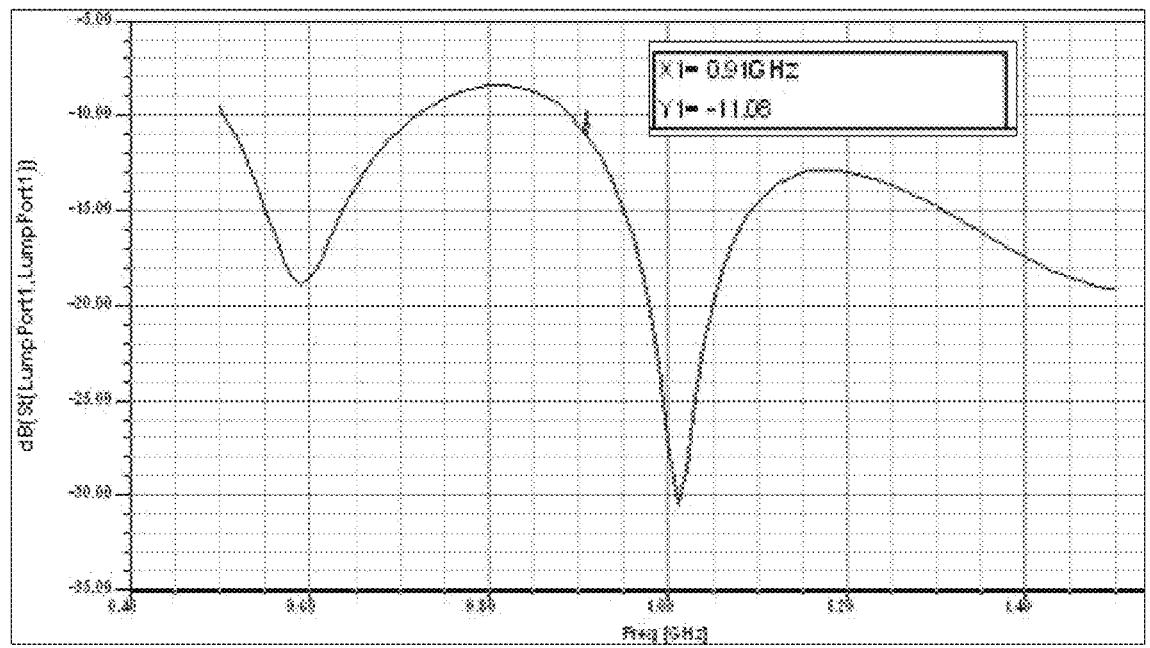
FIG. 1F shows the simulated return loss of an ablation device with an antenna of FIG. 1D.
Figure 1G:
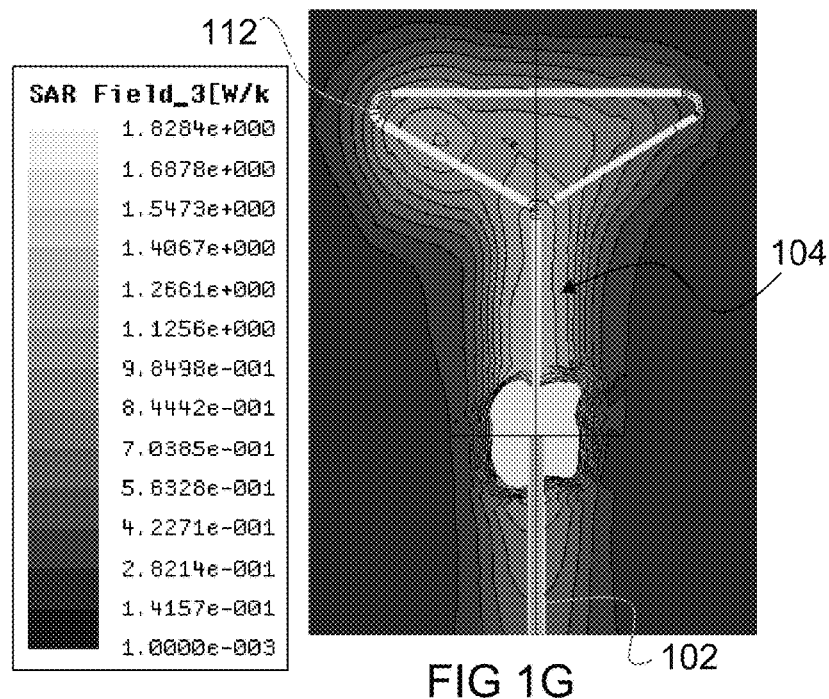
FIG. 1G shows the front view of the SAR profile generated by the antenna of FIG. 1D without center loop.
Figure 1H:
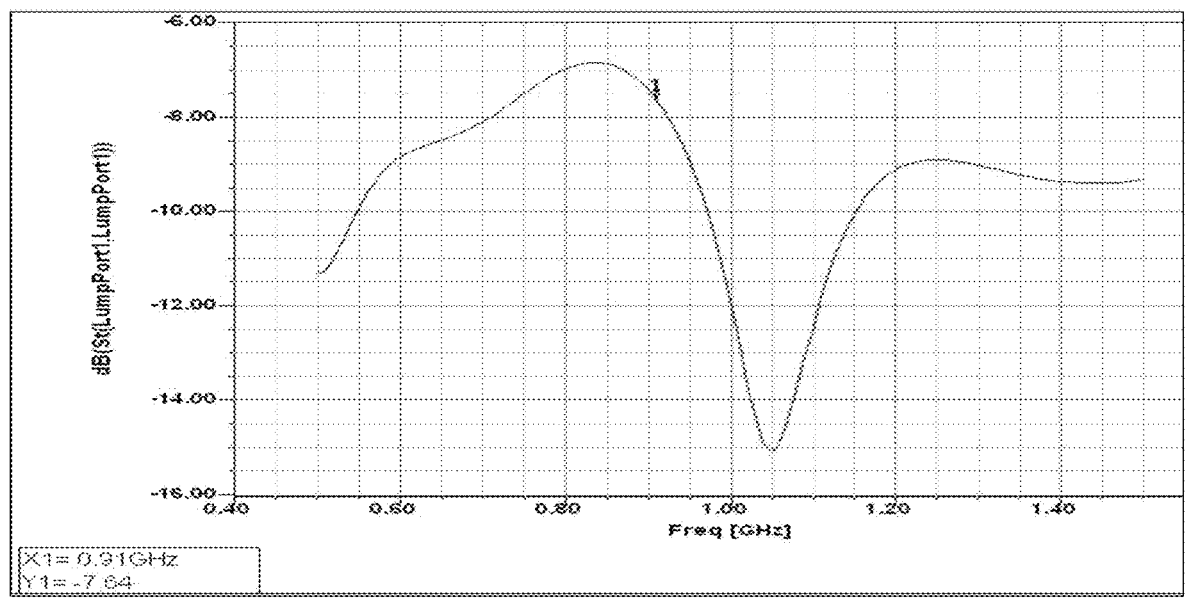
FIG. 1H shows the simulated return loss of an ablation device with the antenna of FIG. 1G.
Figures 1I, 1J:
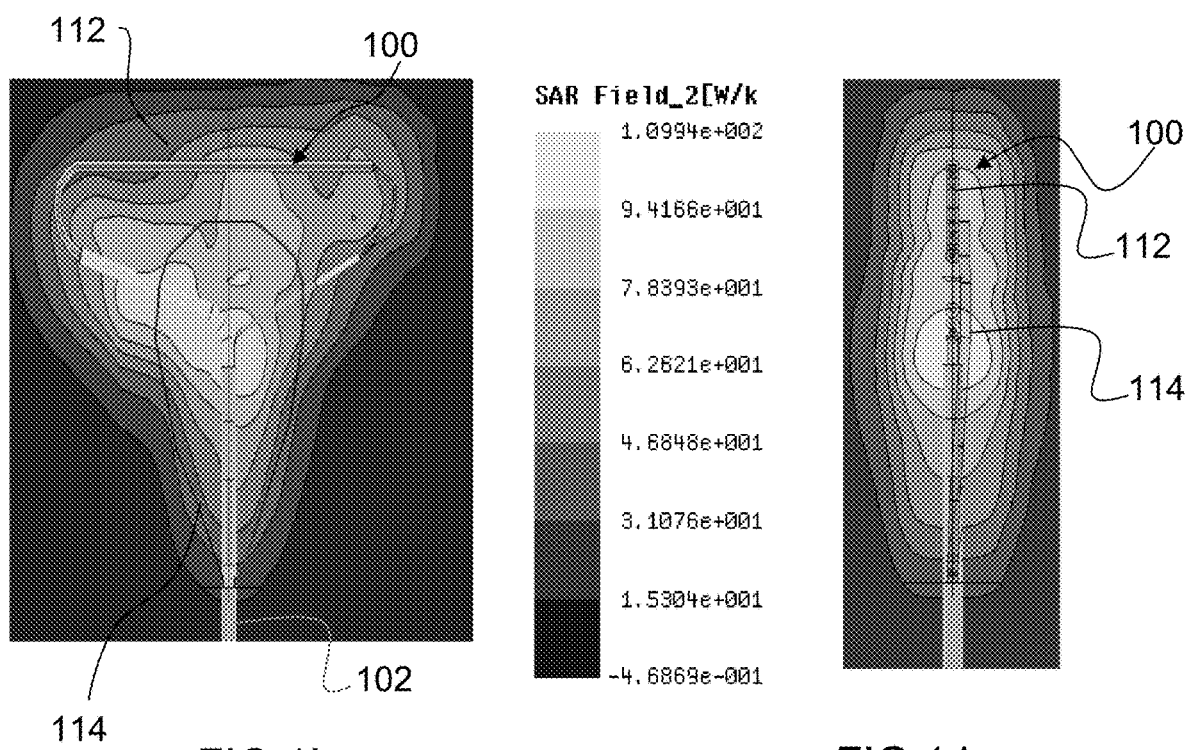
FIGS. 1I and 1J show the front and side views respectively of the SAR profile generated by an antenna with a center loop similar to the antenna of FIGS. 1D and 1E.

FIG. 1F shows the simulated return loss of an ablation device with antenna 104 of FIG. 1D. The simulated return loss shows good matching (about −11 dB) at 915 MHz. FIG. 1H shows the simulated return loss of an ablation device with an antenna of FIG. 1G. The simulation shows a return loss of about −7.5 dB at 915 MHz. Thus, the presence of center loop 114 also improves the matching and increases the power efficiency. In the presence of center loop 114, microwave power is delivered more efficiently to the tissue and not wasted as heat generated within ablation device 100.

Shaping element 114 also increases the frequency range (bandwidth) over which antenna 104 delivers an acceptable performance. If the graphs in FIGS. 1F and 1H are compared, at a cutoff of −10 dB, the acceptable frequency range in the embodiment containing shaping element 114 is more than 0.52 GHz (spanning from approximately 0.88 GHz to more than 1.40 GHz). The acceptable frequency range in the comparable embodiment of FIG. 1G without shaping element 114 is only about 0.18 GHz (spanning from approximately 0.97 GHz to approximately 1.15 GHz). Thus in the first case, a larger frequency range (bandwidth) is available over which antenna 104 delivers an acceptable performance. This in turn allows for a design of antenna 104 wherein minor distortions of antenna 104 during typical clinical use or due to minor manufacturing variations do not significantly affect the performance of antenna 104.

FIGS. 1I and 1J show the front and side views respectively of the SAR profile generated by an antenna with a center loop similar to the antenna of FIG. 1D. The general construction of the embodiment in FIG. 1I is similar to the general construction of the embodiment in FIG. 1D. However, in FIG. 1I, the radius of curvature of the two distal edges of the looped distal region of outer loop 112 is more than the corresponding radius of curvature in FIG. 1D. Further, the length of the substantially linear proximal region of outer loop 112 is less than the corresponding length in FIG. 1D. Also, the design of antenna dielectric 116 on antenna 104 in FIG. 1I is different from the design of antenna dielectric 116 on antenna 104 in FIG. 1D. In one embodiment, antenna dielectric 116 on the proximal region of outer loop 112 is made of a layer of PEEK over a layer of EPTFE. The PEEK layer increases the mechanical strength of the proximal region of outer loop 112. In this embodiment, the antenna dielectric 116 on the looped distal region of outer loop 112 is silicone of varying thickness. The thickness of the silicone antenna dielectric 116 on the more proximal portion of the looped distal region of outer loop 112 may be more than the thickness of silicone antenna dielectric 116 on the more distal portion of the looped distal region of outer loop 112. Outer loop 112 may be made of a silver or gold clad metal such as Nitinol. Center loop 114 may be made of a silver or gold clad metal such as Nitinol. In the embodiment shown in FIGS. 1D and 1E, center loop 114 is not covered with any antenna dielectric 116. Thus the metallic surface of center loop 114 may be exposed to the surrounding. Outer loop 112 and center loop 114 may physically touch each other when deployed in the anatomy as shown in FIG. 1E. The clinical advantages of the shape of the SAR profile of antenna 104 in FIGS. 1I and 1J are similar to the clinical advantages of the SAR profile of antenna 104 in FIGS. 1D and 1E.

FIGS. 1K and 1L show two alternate embodiments of shapes of microwave antenna 104 of ablation device 100. In FIGS. 1K and 1L, center loop 114 is not shown. In FIG. 1K, microwave antenna 104 is roughly diamond shaped. The distal most region of microwave antenna 104 measured along the axis of coaxial cable 102 comprises a smooth corner. The microwave antenna 104 in this embodiment is pre-shaped to form the shape as shown in FIG. 1K. Such a microwave antenna 104 can be collapsed to enable insertion of microwave antenna 104 in a collapsed, low-profile, substantially linear, undeployed configuration though a lumen of a device. In FIG. 1K, microwave antenna 104 is sized and shaped such that when antenna 104 is deployed in the uterine cavity and pushed distally by a user, the distal most region of microwave antenna 104 measured along the axis of coaxial cable 102 is pushed by the uterine fundus and flattened to achieve the configuration as shown by the dashed lines. Thus microwave antenna 104 is converted to a roughly triangular shape that is suited for endometrial ablation. In FIG. 1L, the distal most region of microwave antenna 104 measured along the axis of coaxial cable 102 comprises a smooth arc or curve. The microwave antenna 104 in this embodiment is pre-shaped to form the shape as shown in FIG. 1L. Such a microwave antenna 104 can be collapsed to enable insertion of microwave antenna 104 in a collapsed, low-profile, substantially linear, undeployed configuration though a lumen of a device. In FIG. 1L, microwave antenna 104 is sized and shaped such that when it is deployed in the uterine cavity and pushed distally by a user, the distal most region of microwave antenna measured along the axis of coaxial cable 102 is pushed by the uterine fundus and flattened to achieve the configuration as shown by the dashed lines. Thus microwave antenna 104 is converted to a roughly triangular shape that is suited for endometrial ablation. In an alternate embodiment, microwave antenna 104 has elastic, super-elastic or shape memory ability. In this embodiment, microwave antenna 104 regains its shape after deployment in the uterine cavity through a lumen of a device. Such a microwave antenna 104 may be elastically deformed in the uterine cavity by one or more regions of the uterine cavity. FIG. 1M shows the substantially circular crossection of microwave antenna 104 through plane 1M-1M. FIG. 1N shows two alternate crossections of microwave antenna 104 through plane 1N-1N. In FIG. 1N, one alternate crossection is rectangular while the other alternate cross-section is oval.

Ablation device 100 may comprise a fluid transport lumen. The fluid transport lumen extends from a proximal region of ablation device 100 till a distal region of ablation device 100 that is placed inside the uterine cavity. The fluid transport lumen may be used for one or more of: evacuating liquids or gases from the uterus, introducing liquids inside the uterus such as anesthetics, contrast agents, cauterizing agents, alcohols, thermal cooling agents, a fluid dielectric medium that surrounds antenna 104, antibiotics and other drugs, saline and flushing solutions, introducing gases inside the uterus such as carbon dioxide for distending the uterine cavity or detecting perforation of the uterus, applying suction to collapse the uterine cavity around the antenna 104.

Suction may be applied in the uterine cavity to increase the contact of antenna 104 with the uterine endometrium. When a gas such as carbon dioxide is used for distending the uterine cavity and/or for detecting perforation of the uterus, the gas may be delivered at a pressure between 20-200 mmHg.

Ablation device 100 may comprise a device transport lumen. The device transport lumen may extend from a proximal region of ablation device 100 till a distal region of ablation device 100 that is placed inside the uterine cavity. The device transport lumen may be used for one or more of: introducing one or more elongate diagnostic and/or therapeutic devices in the uterine cavity, introducing ablation device 100 over a guidewire or other introducing device and introducing an imaging or visualization device.

Any of the ablation devices 100 herein may comprise a microwave antenna and/or the positioning devices disclosed in co-pending application Ser. No. 12/603,077 filed on Oct. 21, 2009; and Ser. No. 12/603,134 filed on Oct. 21, 2009. The entire disclosures of each of which are incorporated herein by reference.

In one embodiment, a region of outer loop 112 adjacent to the distal end of coaxial cable 102 is electrically shorted to another region of outer loop 112 adjacent to the distal end of coaxial cable 102.

Center loop 114 may be made of Ag or Au plated Nitinol or stainless steel. Center loop 114 may or may not be pre-shaped. The crossection of center loop 114 may be circular or rectangular or oval. Center loop 114 may be multi-stranded. In one embodiment, center loop 114 is roughly oval in shape and has a width of 13+/−5 mm and a length of about 35+/−8 mm. In one embodiment, center loop 114 is roughly oval in shape and has a width of 13+/−5 mm and a length of about 27.5+/−8 mm. In one embodiment, center loop 114 is roughly oval in shape and has a width of 13+/−5 mm and a length of about 35+/−8 mm. In one embodiment, ablation device 100 further comprises one or more additional elongate metallic conductors or dielectric connected to a region of antenna 104 to confer mechanical stability to antenna 104 as well as to shape the microwave field. Various antennas 104 may be designed using a combination of various elements disclosed herein. Various antennas 104 may be designed using any combination of a radiating element 112 disclosed herein and a shaping element 114 disclosed herein.

In one embodiment, antenna 104 is mechanically deployable. Antenna 104 in this embodiment is user deployable by engaging a mechanical deployment system. The mechanical deployment system in one embodiment is a pullable and releasable pull wire attached to a region of outer loop 112. The pull wire may be made of a metallic or non-metallic e.g. polymeric material. When the pull wire is pulled along the proximal direction, outer loop 112 is distorted. The distortion is such that antenna 104 achieves a working configuration from an initial non-working configuration. Such an embodiment is advantageous since presence of tissue forces are not required for the proper deployment of antenna. This allows the antenna 104 to be made stiffer. One or more pull wires may be attached to one or more regions of antenna 104 to controllably modify the orientation of antenna 104 relative the axis of the distal end of coaxial cable 102. This may be used to position antenna 104 relative to a target tissue in a desired orientation while performing e.g. a laparoscopic procedure. Further, a mechanical deployment system allows the user to get a feedback (e.g. tactile feedback) about the proper deployment of antenna 104. This eliminates the necessity of a post-deployment visualization of antenna 104 to confirm proper deployment. In another example, the mechanical deployment system allows the user to visually observe the extent of displacement of the pull wire which is correlated to the extent of deployment of antenna 104.

Figure 3:
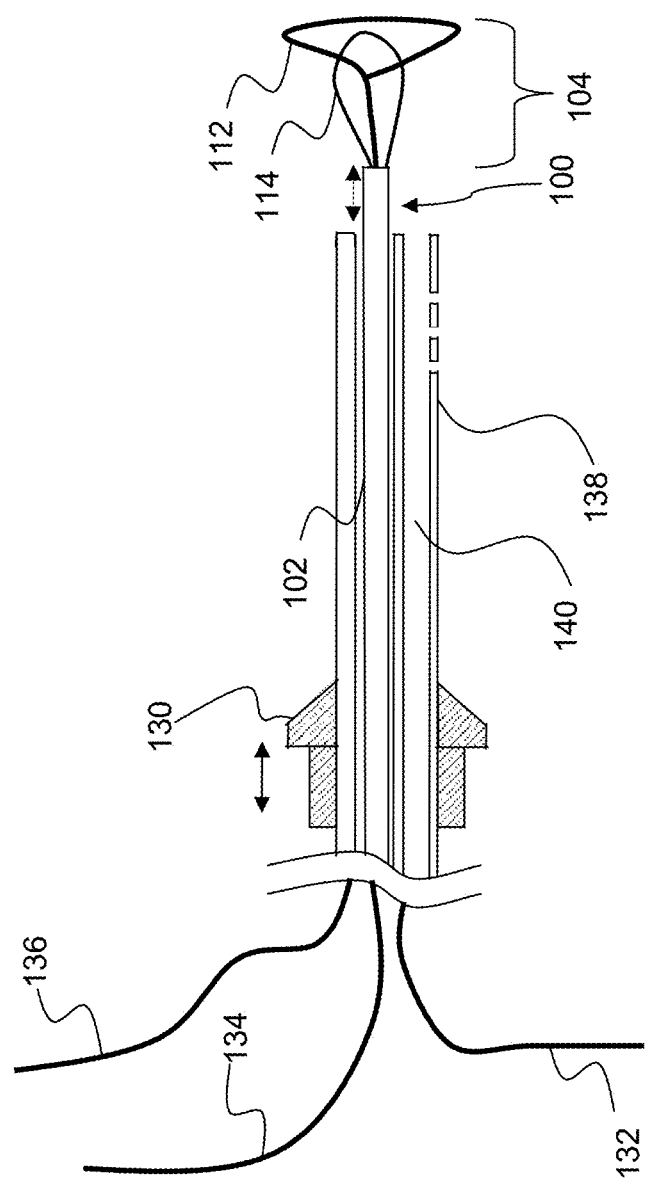
FIG. 3 shows a first embodiment of an ablation system comprising an ablation device slidably introduced within an introducing sheath.

In a method embodiment, ablation device 100 is introduced in a uterine cavity through an introducing sheath 138. FIG. 3 shows an embodiment of an ablation system comprising ablation device 100 slidably introduced within an introducing sheath 138. The antenna 104 is collapsible such that it can be collapsed within a lumen of introducing sheath 138. This reduces the overall profile of antenna 104 such that antenna 104 can be introduced through small openings such as the cervix without needing much or any cervical dilation. This significantly reduces the cost and difficulty of the overall procedure. In one embodiment, ablation device 100 is rotatable within a lumen of introducing sheath 138 to change the angular orientation of ablation device 100 relative to introducing sheath 138. In one embodiment, a lumen of introducing sheath 138 comprises a sealing or locking mechanism such as a rotating hemostasis valve to lock the relative rotational and longitudinal positions of ablation device 100 and introducing sheath 138. The distal end of introducing sheath 138 may comprise an atraumatic tip. The shaft of introducing sheath 138 may be made of a polymeric material. Examples of polymeric materials that can be used include, but are not limited to Nylon, polyethylene, PEEK, PTFE and silicone. One or more portions of introducing sheath 138 may comprise one or more stiffening elements such as jackets or braids or coatings to increase one or more of pushability/column strength, kink resistance and torqueability. One or more portions of introducing sheath 138 may be pre-shaped. Introducing sheath 138 may comprise one or more deflecting or steering elements which may be used to deflect or steer antenna 104. Antenna 104 is deployed by extending the antenna 104 beyond the distal end of introducing sheath 138. The outer surface of introducing sheath 138 comprises one or more distance markings. Such distance markings are useful to insert introducing sheath 138 up to a desired depth in the uterine cavity. In one embodiment, the outer surface of the shaft or the transmission line of ablation device 100 comprises one or more distance markings. The one or more distance markings on the shaft of ablation device 100 are useful to determine the relative positions of the distal ends of the ablation device 100 and introducing sheath 138 within the uterus. In particular, one of the distance markings may be used to determine if the antenna 104 has been fully deployed out of the distal end of introducing sheath 138. A locking mechanism may be provided to lock the position of ablation device 100 relative to the position of introducing sheath 138. In FIG. 3, ablation device 100 comprises an antenna 104. Antenna 104 may be designed using one or more designs or elements disclosed herein. In FIG. 3, antenna 104 comprises a radiating element 112 and a shaping element 114. Examples of radiating elements 112 include, but are not limited to linear or pre-shaped or bent or curved monopole antennas and elements similar to outer loop 112 of FIG. 1A. Examples of shaping elements include, but are not limited to elements similar to metallic center loop 114 of FIG. 1A and dielectric materials. In this embodiment, ablating position 104 is self deploying because of its elasticity or shape memory. Ablation device 100 may comprise one or more pullable or releasable tethers to control the extent of deployment of one or more regions of antenna 104.

Figure 2A:
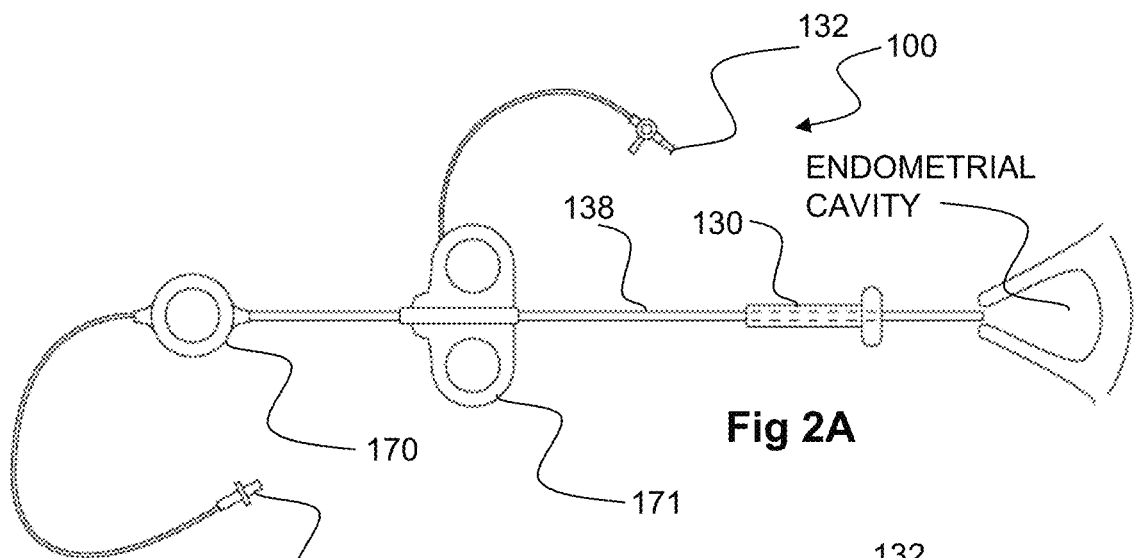
FIGS. 2A-2C show the various steps of a method of using an ablation device for endometrial ablation.
Figure 2B:
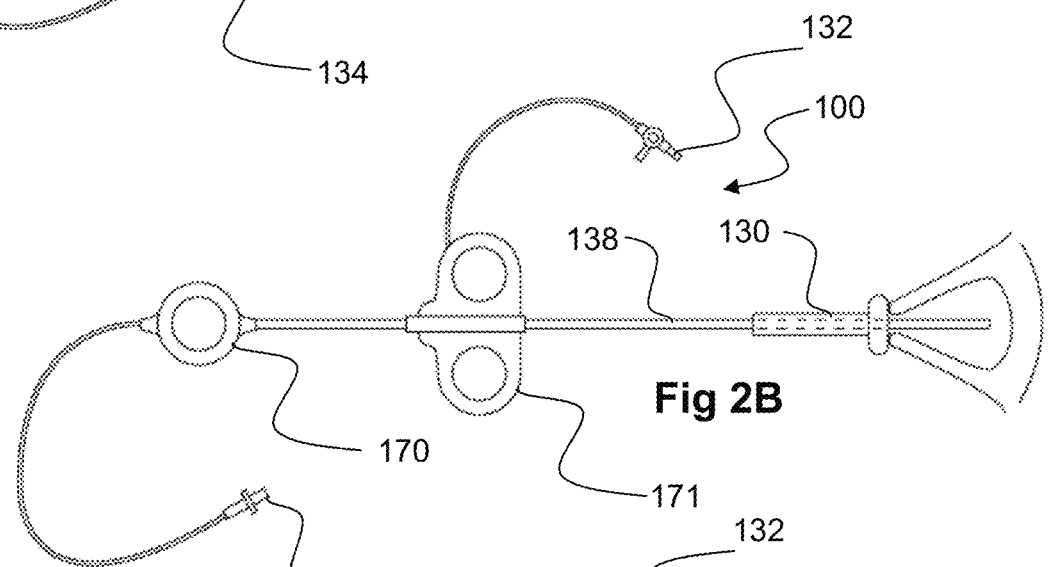
Figure 2C:
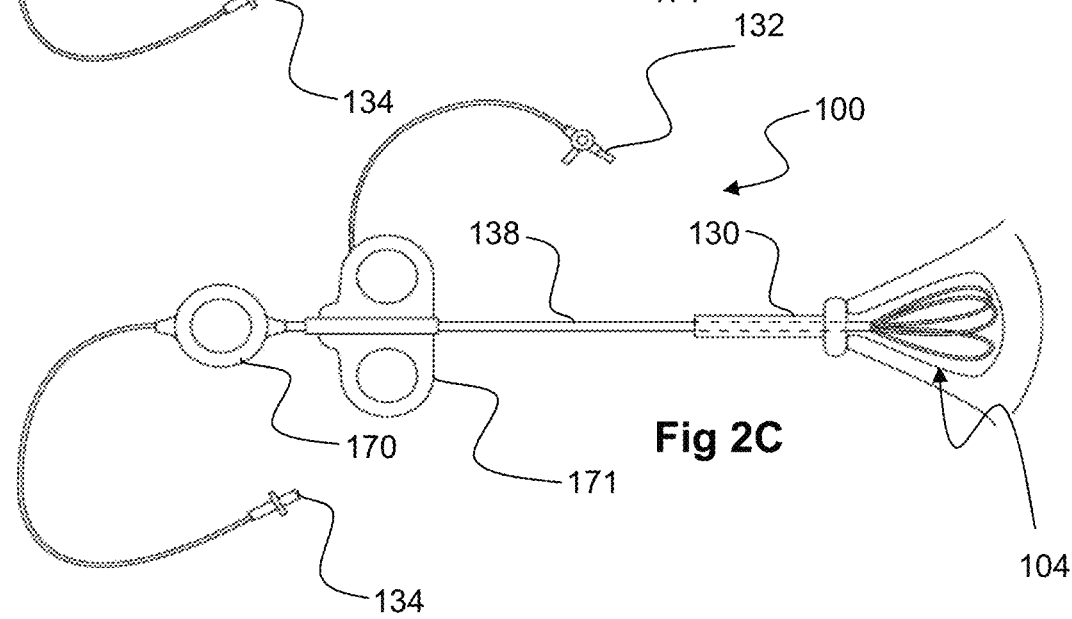

FIGS. 2A-2C show the various steps of a method of using an ablation device for endometrial ablation. In FIG. 2A, ablation device 100 comprises an antenna 104 connected to a transmission line. The proximal end of the transmission line is connected to a proximal handle portion 170 that can be manipulated by the user. A second connection 134 is connected to proximal handle portion. In one embodiment, second connection 134 comprises a transmission line that connects antenna 104 to a source of energy. Ablation device 100 is slidably enclosed in a substantially linear, low profile, undeployed, collapsed configuration within a lumen of an introducing sheath 138. Antenna 104 can be extended out of the distal end of the introducing sheath 138 as shown in FIG. 2C. A slidable stopper 130 is located on the outer surface of introducing sheath 138. The position of stopper 130 on sheath 138 can be adjusted by the user. A proximal region of sheath 138 comprises a distal handle potion 171 that cooperates with the proximal handle portion 170 to change the relative positions of ablation device 100 and sheath 138. In the embodiment shown, both proximal handle portion 170 and distal handle portion 171 can be operated by a user with a single hand. A lumen of sheath 138 is in fluid connection with a port that forms a first connection 132. First connection 132 may be connected to any external modality disclosed herein. In one embodiment, first connection 132 is designed to connect to a source of suction. Thus the user can apply suction inside the uterine cavity using the combination of ablation device 100 and sheath 138. In one method embodiment, the uterine cavity length is measured. Thereafter, the position of stopper 130 on sheath 138 is adjusted based on the uterine cavity length. Thereafter, sheath 138 containing ablation device 100 is introduced inside the uterine cavity until shopper 130 touches the cervix as shown in FIG. 2B. Stopper 130 enables the distal end of sheath to be positioned at a desired depth inside the uterine cavity. Stopper 130 may also act as a seal to create a fluid tight seal in the cervix. In FIG. 2C, proximal handle portion 170 and distal handle portion 171 are brought together such that antenna 104 is deployed inside the uterine cavity. This causes antenna 104 to emerge out of the distal end of sheath 138 and be positioned inside the uterine cavity in a substantially planar, deployed, un-collapsed configuration. In one embodiment, the distance by which proximal handle portion 170 and distal handle portion 171 are brought together is based on a uterine cavity dimension. Thereafter, energy such as microwave energy is delivered to the endometrium for ablating the endometrium. Thereafter, proximal handle portion 170 and distal handle portion 171 are moved apart such that antenna 104 is enclosed inside sheath 138. Thereafter, sheath 138 and ablation device 100 are removed from the anatomy.

In FIG. 3, the ablation system comprising ablation device 100 introduced within an introducing sheath 138 is connected to an external system by one or more connections. Examples of such connections include, but are not limited to a first connection 132 to a source of suction (e.g. a suction line), a second connection 134 to a source of microwave energy (e.g. a microwave generator) and a third connection 136 to an infusion device (e.g. a syringe). In one embodiment, the microwave generator has an interface to enable the user to adjust the microwave power delivered to ablation device 100. For example, the microwave power may be adjustable in increments of 5 W (5 W, 10 W, 15 W, etc). In one embodiment, the microwave generator has an interface to enable the user to adjust the duration of microwave power delivery to ablation device 100. For example, the direction of microwave power delivery may be adjustable in increments of 5 s (5 s, 10 s, 15 s, etc). An embodiment of the microwave generator designed for the various studies disclosed herein was compact and weighed about 30 pounds. Thus the entire ablation system is portable. It can easily be used in the office setting or an operating room (OR) setting as desired.

Introducing sheath 138 may comprise a fluid transport lumen 140. The fluid transport lumen 140 may extend from a proximal region of introducing sheath 138 till a distal region of introducing sheath 138 that is placed inside the uterine cavity. The fluid transport lumen 140 may be used for one or more of: evacuating liquids or gases from the uterus, introducing liquids inside the uterus such as anesthetics, contrast agents, cauterizing agents, antibiotics and other drugs, saline and flushing solutions, introducing gases inside the uterus such as carbon dioxide for distending the uterine cavity or detecting perforation of the uterus and applying suction to collapse the uterine cavity around the antenna 104. Suction may be applied in the uterine cavity to increase the contact of antenna 104 with the uterine endometrium. When a gas such as carbon dioxide is used distending the uterine cavity and/or detecting perforation of the uterus, the gas may be delivered at a pressure between 20-200 mmHg.

Introducing sheath 138 may comprise a device transport lumen. The device transport lumen may extend from a proximal region of introducing sheath 138 till a distal region of introducing sheath 138 that is placed inside the uterine cavity. The device transport lumen may be used for one or more of: introducing one or more elongate diagnostic and/or therapeutic devices in the uterine cavity, introducing ablation device 100 over a guidewire or similar introducing device and introducing an imaging or visualization device.

In one method embodiment, a uterine sound is used to sound the uterus to obtain information about the depth and the position of the uterine cavity and the depth and the position of the cervical canal. Thereafter, ablation device 100 located within introducing sheath 138 is introduced into the uterine cavity. Antenna 104 is completely within a lumen of introducing sheath 138 to reduce the profile of antenna 104. Introducing sheath 138 is navigated within the uterine cavity such that the distal end of introducing sheath 138 touches or is substantially adjacent to the fundus of the uterus. Thereafter, antenna 104 is deployed within the uterine cavity by withdrawing introducing sheath 138 while maintaining the position of ablation device 100. In absence of external forces on antenna 104, antenna 104 re-establishes its original shape due to the elastic and/or super-elastic nature of one or more regions of antenna 104. Thereafter, ablation device 100 is used to ablate the uterine endometrium. Thereafter, ablation device 100 is removed from the uterus. In one embodiment, this is done by withdrawing ablation device 100 proximally while maintaining the position of introducing sheath 138 to collapse the antenna 104 inside introducing sheath 138. In an alternate embodiment, ablation device 100 is pulled proximally to collapse antenna 104 against the cervical canal and the cervix and thereafter removed from the uterus.

In one embodiment, a space or gap between the outer surface of ablation device 100 and a lumen of introducing sheath 138 acts as a fluid and/or device transport lumen.

Ablation device 100 and/or introducing sheath 138 may comprise a stopper 130 located on the outer surface of ablation device 100 and/or introducing sheath 138. Stopper 130 is designed to abut against the external portion of the cervix and thereby limit the insertion depth of ablation device 100 and/or introducing sheath 138. The position of stopper 130 relative to the position of the shaft of ablation device 100 and/or introducing sheath 138 may be adjustable. The position of stopper 130 relative to the position of the shaft of ablation device 100 and/or introducing sheath 138 may be reversibly lockable. In one method embodiment, the desired depth of insertion of ablation device 100 and/or introducing sheath 138 is determined by one or more of uterine sounding, hysteroscopy and ultrasonography. Thereafter, the position of stopper 130 relative to the distal end of ablation device 100 and/or introducing sheath 138 is adjusted. Thereafter, ablation device 100 is inserted into the uterine cavity. Stopper 130 limits the depth of insertion of the distal end of ablation device 100 and/or introducing sheath 138 thereby reducing the risk of uterine perforation and ensuring optimal placement of antenna 100 relative to the target tissue. Stopper 130 may also act as an external seal to create a fluid tight seal of the cervical canal. In the embodiment in FIG. 3, ablation device 100 comprises an insertion limiting feature such as stopper 130 to limit the insertion depth of ablation device 100.

In another embodiment, ablation device 100 comprises an antenna 104 that comprises a non-linear radiating element 112 and a non-linear shaping element 114. In this embodiment, both radiating element 112 and shaping element 114 are each connected to separate tethers. The tethers can be manipulated by the user to change the shape and/or orientation of one or more of: radiating element 112 and shaping element 114 in the anatomy. In this embodiment, radiating element 112 may be made of a length of a conductor coated with a dielectric material. Shaping element 114 may be made of multiple strands of outer conductor 106 that are twisted together.

Figure 4:
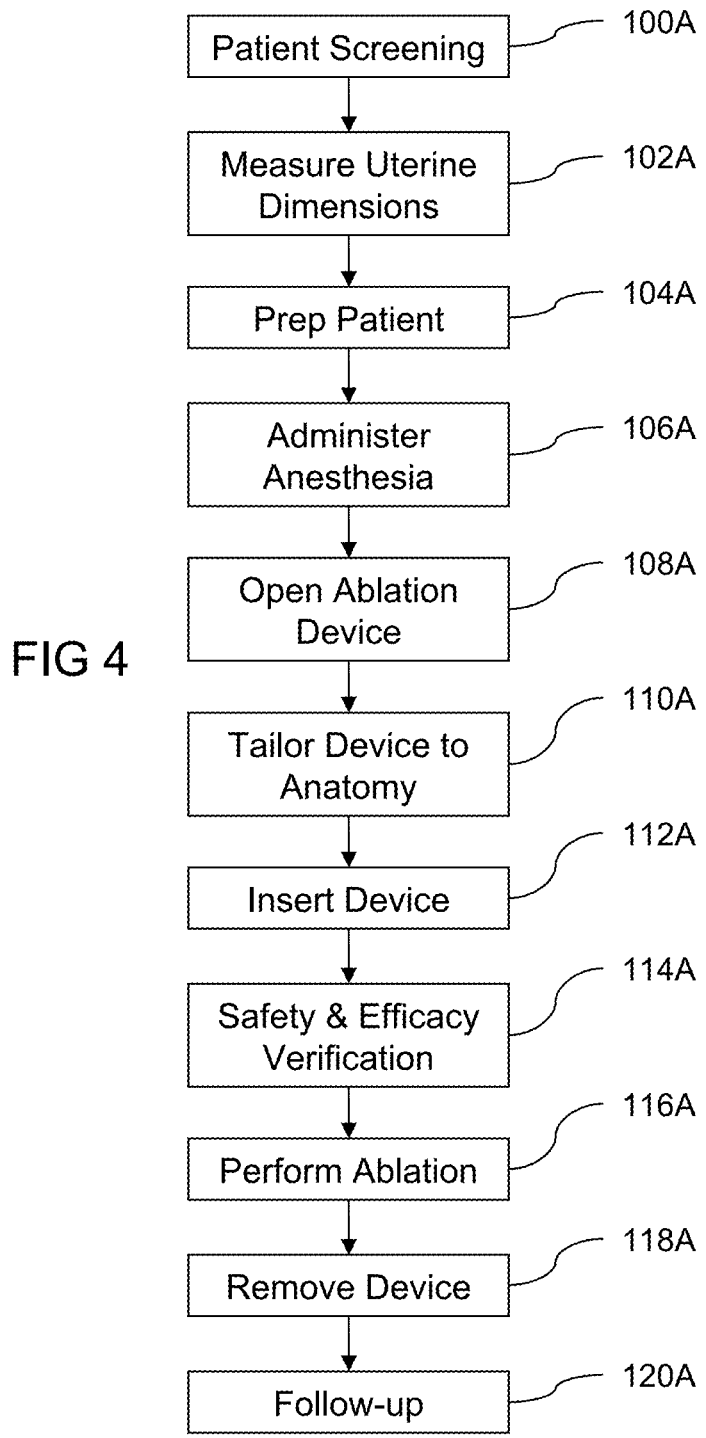
FIG. 4 illustrates the key steps of an embodiment of a method of endometrial ablation.

FIG. 4 illustrates the key steps of an embodiment of a method of endometrial ablation. At step 100A, the patient is screened to determine if she is suitable for ablation. This may include one or more of taking medical history, ultrasonography (with or without saline infusion), endometrial biopsy and asking the patient her treatment preferences. At step 102A, uterine dimensions are measured. The uterine dimensions measured may be selected from the group comprising: uterine cavity length and/or width, uterine cavity position, uterine cavity orientation, cervical canal length and/or width and cervical canal position. This may be done by one or more of A. ultrasonography (abdominal or transvaginal) with or without contrast agent or saline in the endometrial cavity, B. pre-procedure MRI with or without a contrast agent or saline in the endometrial cavity, C. sounding the uterus by a standard uterine sound or a Wing Sound-like device that not just measures the uterine cavity and cervical cavity length, but also the uterine cavity width in the cornual region and D. performing a bimanual examination or palpating the uterus to get an idea of the approximate dimensions and the orientation. At step 104, the patient is prepped for the procedure. The patient may be positioned in the standard position used for gynecological examination such as the dorsal lithotomy position using stirrups. The patient may be draped. The patient is advised about what to expect during and after the procedure. A speculum may be inserted. The cervix may be grasped with a tenaculum if necessary. At step 106A, anesthesia if needed is administered to the patient. In one embodiment, oral pain medications e.g. NSAIDs are given a few hours before the procedure. At step 106A, a para-cervical block is placed. Since this procedure requires minimal anesthesia, it may easily be done in the office. The slim and flexible nature of several embodiments of antennas 104 disclosed herein may allow the physician to perform an ablation without any anesthesia. If the patient wishes, the procedure may be carried out in an ambulatory surgical center or in an operating room. Also, the physician may decide to in an ambulatory surgical center or in an operating room. For example, if the patient is morbidly obese, then the physician may decide to perform the procedure in an OR. Thus, in step 106A, conscious sedation or general anesthesia may be administered. Slight cervical dilation if necessary may be done after step 106A. In step 108A, ablation device 100 is opened from its package. In one embodiment, various ablation devices 100 of varying sizes and shapes are provided. For example, a set of three ablation devices 100 may be provided wherein each ablation device 100 is adapted to treat a uterus lying within a particular size and shape range. The user may use the uterine dimension data from step 102A to select the appropriate ablation device 100 for the ablation. Alternately, a single ablation device 100 is designed to be usable for all patients. At step 110A, ablation device 100 is tailored to the anatomy. In one embodiment, one or more of ablation 100 device size and shape parameters may be changed by the physician to tailor ablation device 100 to the patient's anatomy. For example, a deployed length and/or width of ablation device 100 may be changed. The ablation device 100 may be tailored to account for one or more of: uterine cavity length and/or width, uterine cavity position, uterine cavity orientation, cervical canal length and/or width and cervical canal position. In one embodiment, the position of stopper 130 is adjusted on the shaft of ablation device 100. At step 112A, ablation device 100 is inserted trans-cervically into the uterine cavity. The ablation device 100 is positioned such that antenna 104 is located within the uterine cavity. In one embodiment, ablation device 100 is inserted in a collapsed configuration for insertion through a narrow opening (e.g. <4 mm in diameter). When the distal region of ablation device 100 reaches the target location, antenna 104 is un-collapsed or deployed in the working configuration. In step 114, the critical pre-ablation parameters needed for the safety and efficacy of the procedure are verified. For example, placement of antenna 104 in the uterine cavity may be confirmed. The placement and/or the orientation of antenna 104 may be verified by imaging or by accurately calculating the position and/or the orientation of the device. A perforation detection test may be performed to rule out ablation device-caused or naturally-present perforations of the uterus. This test may be carried out by detecting leaks of a fluid introduced into the uterine cavity. The proper contact of antenna 104 with the surface of the endometrium may be determined by imaging (e.g. ultrasound imaging) or other method such as measuring a physical parameter such as the temperature or impedance of adjoining tissue. In one embodiment, a vaginoscopic technique is used to insert ablation device 100 into the anatomy. In a vaginoscopic technique, a type of endoscope is used to visualize the vaginal canal. In this technique, a speculum is not used. Further, in this technique, a tenaculum may not be needed to grasp the cervix. At step 116A, the endometrium is ablated. The ablation parameters may be automatically selected by the microwave generator after the user enters some patient specific data such as anatomical data. Alternately, the user may calculate the ablation parameters such as the magnitude of power delivery, waveform, ablation time, etc. based on specific inputs such as patient's anatomical data. The ablation parameters may then be fed into the generator. The end point of the ablation may be determined automatically by the microwave generator or the user may decide an ablation endpoint based on a protocol. One or more parameters may be used to calculate the end point and/or terminate the ablation. Examples of such parameters include, but are not limited to tissue temperature at one or more places, ablation time, ablation power, impedance of tissue at one or more places, patient's anatomical parameters, etc.

In step 118A, after the ablation is finished, the antenna 104 is collapsed and removed from the uterus. Thereafter, in step 120A, the patient is followed up post-procedure for a certain time. The patient may be given specific instructions on the symptoms of some ablation complications so that the patient can contact the physician immediately if she experiences those symptoms post-procedure.

It is not necessary that all of the abovementioned steps are performed during the method. One or more steps may be added, deleted or modified as per the clinical requirements.

Instead of ablation, the method and devices herein may be used for other applications as disclosed elsewhere. The procedures disclosed herein may be performed under real-time monitoring e.g. by direct visualization, hysteroscopy, ultrasound, radiologically, by laparoscope, etc.

Figure 5A:
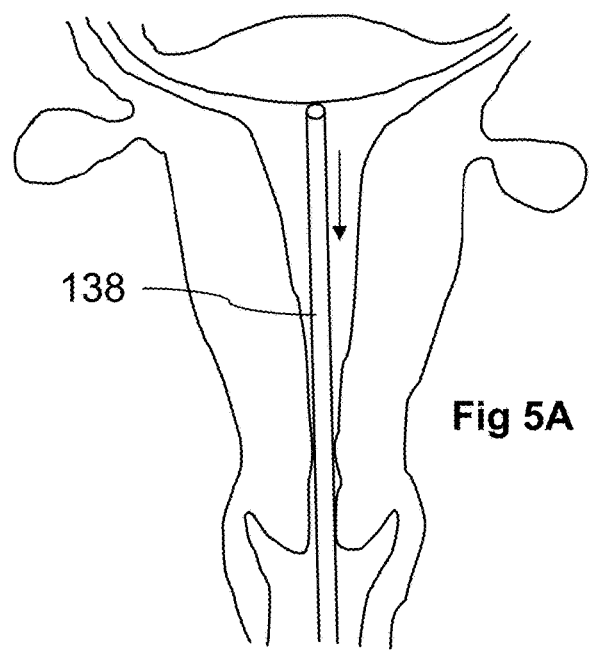
FIGS. 5A-5E illustrate the key steps of ablating uterine endometrium to treat menorrhagia using a collapsible microwave ablation antenna.
Figure 5B:
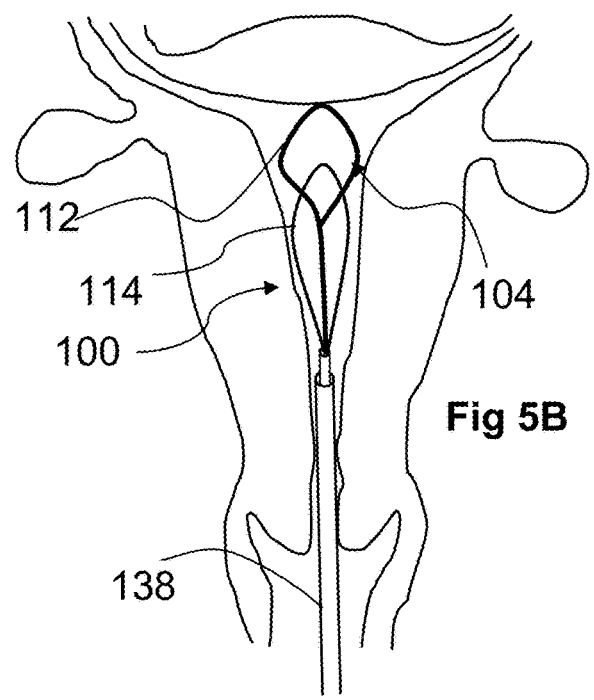
Figure 5C:
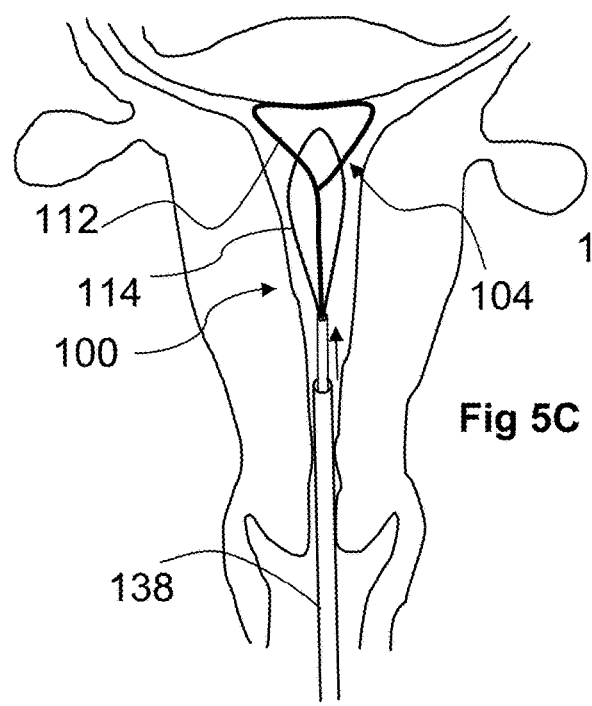
Figure 5D:
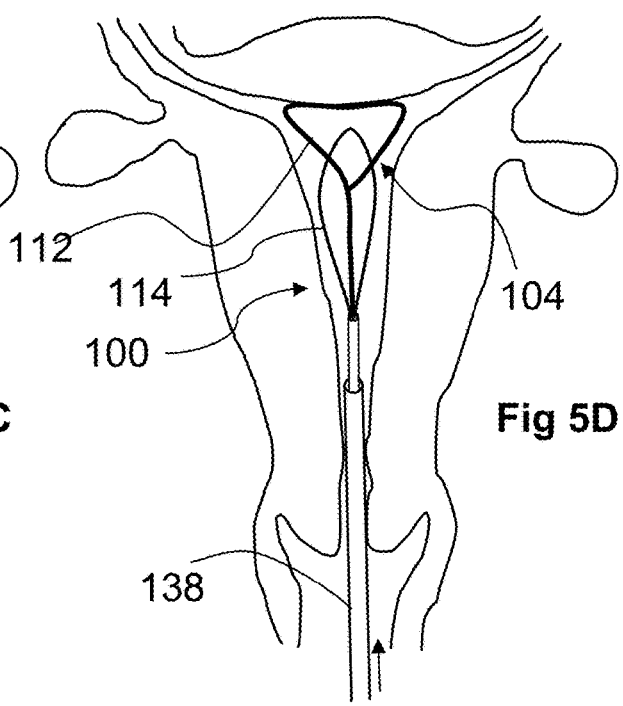
Figure 5E:
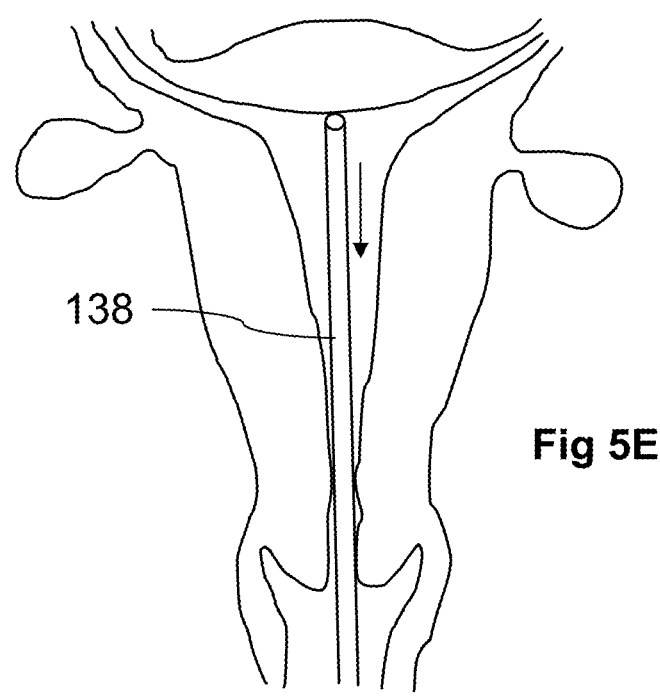

FIGS. 5A-5E illustrate the key steps of ablating uterine endometrium to treat menorrhagia using a collapsible microwave ablation antenna. Although only a few key steps are illustrated in FIGS. 5A-5E, it is emphasized that any other method steps disclosed elsewhere in the specification may be added to or substituted for a step in FIGS. 5A-5E. In FIG. 5A, ablation device 100 located within introducing sheath 138 is introduced into the uterine cavity such that the distal end of introducing sheath 138 touches or is substantially adjacent to the fundus of the uterus. In one method embodiment, anatomical information about uterine cavity and cervical canal lengths and positions are obtained prior to the step in FIG. 5A. This anatomical information is used to position the distal end of introducing sheath 138 in the uterine cavity. Further, in the step shown in FIG. 5A, introducing sheath 138 is withdrawn in the proximal direction while maintaining the position of ablation device 100. This deploys antenna 104 in the uterine cavity as shown in FIG. 5B. After antenna 104 is deployed in the uterine cavity, ablation device 100 is displaced in the distal direction by a calculated amount in step 4D. This displacement causes the distal most region of antenna 104 to be pressed against the uterine fundus. This in turn causes antenna 104 to flatten and achieve a working configuration. In one embodiment, the amount of displacement of ablation device 100 in the distal direction is calculated based on an anatomical dimension such as a uterine dimension (e.g. the length of the uterine cavity). Microwave antenna 104 of antenna 104 is longitudinally compressible similar to the embodiments shown in FIGS. 6A and 6B to achieve a working configuration. Ablation device 100 is placed such that antenna is longitudinally compressed by the fundus of the uterus and is in the working configuration as shown in FIG. 5C. It should be noted that in the embodiment shown in FIG. 5C, the deployed antenna 104 extends over a majority of (more than half of) the uterine cavity. More specifically, the deployed maximum width of antenna 104 is greater than half of the maximum width of the uterine cavity and more specifically, greater than three fourths of the maximum width of the uterine cavity. Also, the deployed length of antenna 104 is more than half the length of the uterine cavity and more specifically, greater than three fourths of the length of the uterine cavity. Further, in the step shown in FIG. 5C, ablation device 100 is used to ablate the uterine endometrium. Thereafter, in the step shown in FIG. 5D, introducing sheath 138 is advanced distally over antenna 104. This collapses antenna 104 and causes ablation device 100 to be enclosed within introducing sheath 138. Thereafter, in the step shown in FIG. 5E, introducing sheath 138 along with ablation device 100 is removed proximally from the anatomy.

It should be noted that the simple design of ablation device 100 reduces the device cost. Further, such a simple endometrial ablation procedure has a low total procedure cost. This enables a wide variety of physicians in the US and elsewhere to use this technique. This technique can easily be used in a physician's office which reduces the procedure cost even more.

Ablation device 100 disclosed herein may be inserted and/or used blindly i.e. without using any additional imaging modality.

Alternately, ablation device 100 disclosed herein may be inserted and/or used under hysteroscopic guidance. Thus, hysteroscopic microwave endometrial ablation, if desired, is possible with the various devices and methods disclosed herein. In one embodiment, a slim diagnostic hysteroscope is co-introduced through the cervix along with an ablation device 100 into the uterine cavity. The slim diagnostic hysteroscope is then used to visualize and guide the placement of ablation device 100 in the uterine cavity. Thereafter, the diagnostic hysteroscope is partially or full withdrawn from the anatomy. Thereafter, an ablation procedure is performed by ablation device 100. In another method embodiment, ablation device 100 is introduced in the anatomy through a channel of a hysteroscope or resectoscope sheath. The ablation devices 100 disclosed herein can be made sufficiently low profile to enable their introduction though a channel (e.g. a 7 French channel) of a hysteroscope or resectoscope sheath. The hysteroscope or resectoscope sheath may be partially or fully withdrawn from the anatomy before an ablation procedure by ablation device 100.

Alternately, ablation device 100 disclosed herein may be inserted and/or used under ultrasonic guidance. The ultrasonic guidance may be trans-abdominal ultrasound, trans-vaginal ultrasound or intra-uterine ultrasound.

Alternately, ablation device 100 disclosed herein may be inserted and/or used under radiological guidance. In one embodiment, ablation device 100 is used under X-ray or fluoroscopic guidance. Ablation device 100 may comprise one or more radiopaque markers to enable the visualization of one or more regions of ablation device 100 under X-ray or fluoroscopic guidance.

Alternately, ablation device 100 may comprise a visualization modality or means for coupling to a visualization modality. In one embodiment, the visualization modality (e.g. fiberoptic fibers or other optical imaging modality, ultrasound catheter, etc.) may be embedded in a wall of ablation device 100 and/or introducing sheath 138. In another embodiment the visualization modality (e.g. fiberoptic fibers or other optical imaging modality, ultrasound catheter, etc.) may be introduced through a lumen of ablation device 100.

Ablation device 100 may comprise one or more gas or liquid inflatable balloons for doing one or more of positioning antenna 104, providing a cooling modality, enabling better contact of antenna 104 with target tissue and deploying antenna 104.

Figure 6A:
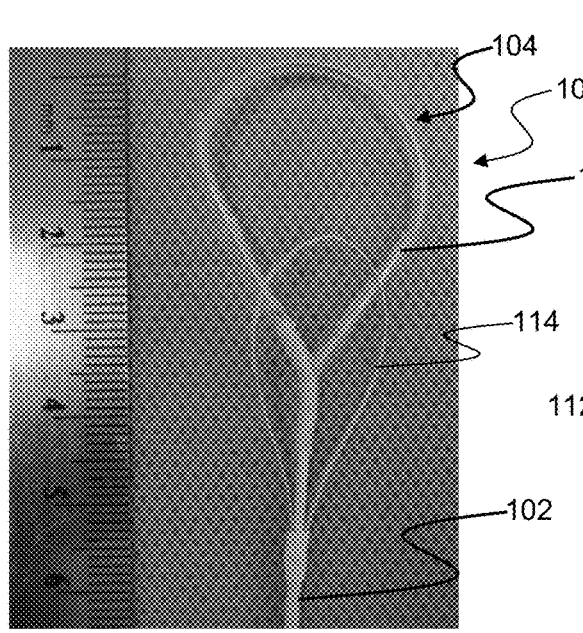
FIG. 6A shows a longitudinally un-constrained and laterally un-collapsed configuration of an embodiment of a microwave antenna.

FIG. 6A shows a longitudinally un-constrained and laterally un-collapsed configuration of an embodiment of a microwave antenna. In FIG. 6A, ablation device 100 comprises an antenna 104 comprising an outer loop 112 and a metallic center loop 114. Outer loop 112 in this configuration is in a more oval shape. The maximum lateral width dimension of antenna 104 is about 2.7 cm. The lateral width of center loop 114 is 1.6 cm+/−0.6 cm and the longitudinal length of center loop 114 is about 5.5 cm+/−1 cm.

Figure 6B:
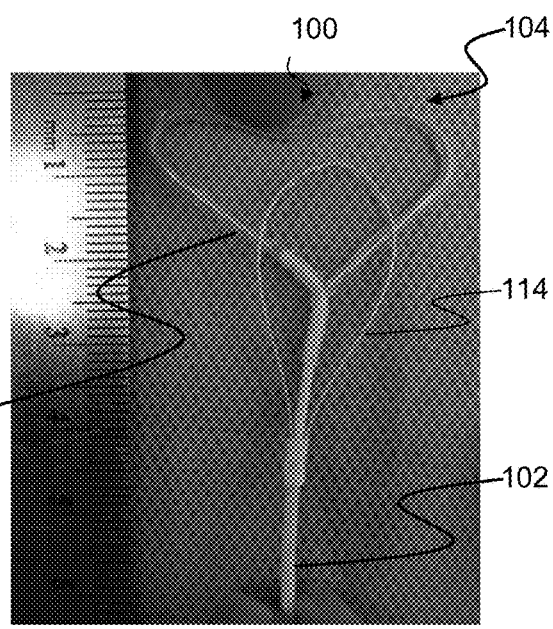
FIG. 6B shows a longitudinally constrained and laterally un-collapsed working configuration of the embodiment of a microwave antenna shown in FIG. 6A.

FIG. 6B shows a longitudinally constrained and laterally un-collapsed working configuration of the embodiment of a microwave antenna shown in FIG. 6A. In FIG. 6B, an external force is used to distort the distal most portion of antenna 104. In FIG. 6B, the distal most portion of antenna 104 was pressed using a finger to demonstrate the distortion of the shape of outer loop 112 from a more oval shape to a more triangular shape as shown. The maximum lateral width dimension of outer loop 112 is now about 3.5 cm. The longitudinal length of antenna 104 from the distal end of coaxial cable 102 till the distal most portion of antenna 104 is about 3.8 cm. This simulates the distortion that antenna 104 experiences by the fundus during actual clinical use in endometrial ablation. The configuration shown in FIG. 6B is the working configuration of antenna 104 in which antenna 104 can be used for endometrial ablation. Thus antenna 104 is capable of existing in three configurations: a first undeployed configuration in which antenna 104 is laterally compressed for insertion through a lumen or opening, a second deployed configuration in which antenna 104 is deployed in the anatomy and is longitudinally un-constrained and laterally un-collapsed in the absence of significant external distorting forces on antenna 104 and a third deployed configuration in which antenna 104 is longitudinally constrained and laterally un-collapsed in the presence of external distorting forces on antenna 104. The third configuration is the actual working configuration.

Figure 6C:
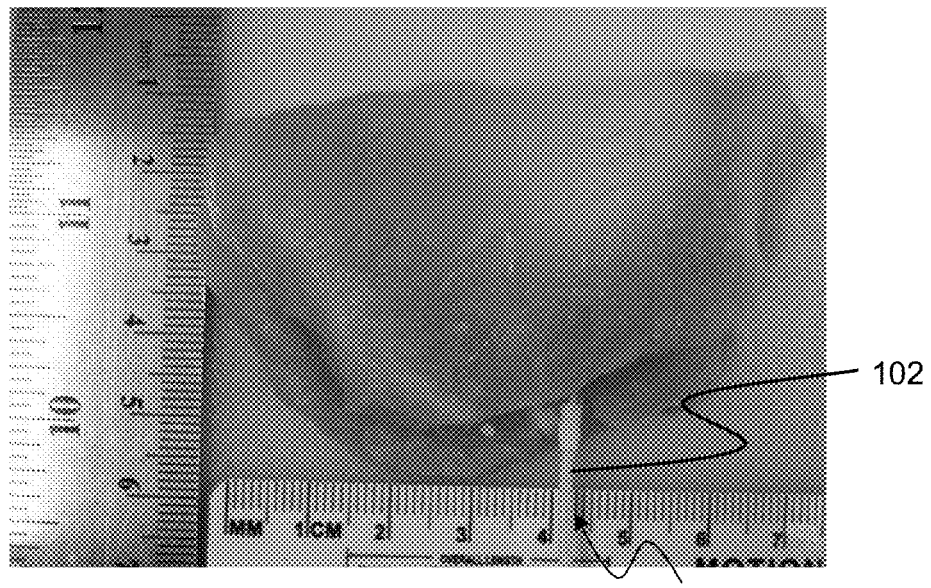
FIG. 6C shows the placement of the microwave antenna of FIGS. 6A and 6B in a folded piece of tissue.

FIG. 6C shows the placement of the microwave antenna of FIGS. 6A and 6B in a folded piece of tissue. In FIG. 6C, a slab of porcine muscle tissue maintained at 37 degrees C. was folded over once. The cavity enclosed by the tissue fold approximately simulates the uterine cavity. Thereafter, antenna 104 of FIGS. 6A and 6B was inserted to a sufficient depth such that the distal most region of antenna 104 is distorted by the porcine tissue to achieve the working configuration as shown in FIG. 6B. Thereafter, the porcine tissue was ablated. The time of power delivery was less than two minutes. Thus endometrial ablation protocols may be designed that ablate a sufficient amount of endometrium in less than tow minutes. In FIGS. 6A and 6B, the ablation was done for 90 s with a delivery of 40 W of microwave power from a microwave generator at 0.915 GHz. Although in this experiment, a constant power of 40 W was used throughout the ablation procedure; in clinical use the magnitude of power delivery by the microwave generator may not be constant throughout the ablation procedure.

In one embodiment, the magnitude of power delivered by ablation device 100 is varied with time during an ablation. In one such embodiment, a higher power is delivered during the first stage of the ablation. Thereafter, the power delivery in the subsequent stages of the ablation is lowered. In one embodiment, the power delivery in the subsequent stages of the ablation is lowered when tissue temperature reaches a desired level e.g. 80 C. In this embodiment, the power delivery may be lowered to maintain the tissue temperature at or below the desired level for a desired time. The power delivery may also be lowered to maintain the temperature of the uterine serosa at or below a desired safe limit during the ablation. In another embodiment, the power delivery in the subsequent stages of the ablation is lowered after a specified time. In one embodiment, the microwave generator is capable of automatically adjusting the magnitude of power delivery based on one or more of: (i) a pre-programmed therapy cycle and (ii) a feedback obtained during the ablation. Examples of pre-programmed therapy cycles include, but are not limited to: a 50% on-50% off duty cycle; a 70% on-30% off duty cycle and cycles wherein the magnitude of power delivery is varied with time. The relative proportion of the on-time and off-time during a duty cycle may be varied though the ablation. The on-time and off-time of a duty cycle may be synchronized with one or more of pulsatile blood flow and a cooling modality. Examples of parameters that can be used for feedback during the procedure include, but are not limited to: temperature, impedance, blood flow, tissue viability, tissue electrical signals (e.g. EKG, EEG, etc.) and tissue characteristics.

In any of the methods disclosed herein, the water content of tissue volume or a surface may be locally modified e.g. by injecting or introducing an aqueous solution. The aqueous solution may be heated up due to absorption of microwave energy. The heated aqueous solution then acts as an additional ablating modality. The heated aqueous solution may flow and conform to irregular regions of target tissue and thus complement the abative action of antenna 104.

If we assume that about 85% of the total microwave energy delivered by the microwave generator is ultimately delivered by antenna 104 to tissue, the total energy delivered to tissue is about 3,000 Joules. Since the tissue used in FIG. 6C is designed to simulate uterine endometrial tissue, endometrial ablation protocols may be designed that involve the delivery of about 3,000 Joules of microwave energy to the endometrium. Further, protocols of endometrial ablation may be designed that deliver less than 3,000 Joules of microwave energy to the endometrium. This can be done for example, by pre-treatment of the uterus, by scheduling the patient for the ablation just after she has a menstrual period, etc.

In FIG. 6B, the total area of generally flattened antenna 104 in its working configuration is about 6.7 square centimeters. Thus, the microwave energy delivered by antenna 104 is delivered to two opposite tissue surfaces, each measuring about 6.7 square centimeters. Again, if we assume that about 85% of the total microwave energy delivered by the microwave generator is ultimately delivered by antenna 104 to tissue, the total power delivered to tissue is about 2.5 Watts per square centimeter of tissue. Further, protocols of endometrial ablation may be designed that achieve the desired clinical outcome while delivering less than 2.5 Watts of microwave power per square centimeter of endometrial surface. This can be done for example, by hormonal pre-treatment of the uterus, by a mechanical pre-treatment of the uterus by D&C, by scheduling the patient for the ablation just after she has a menstrual period, etc.

Figure 6D:
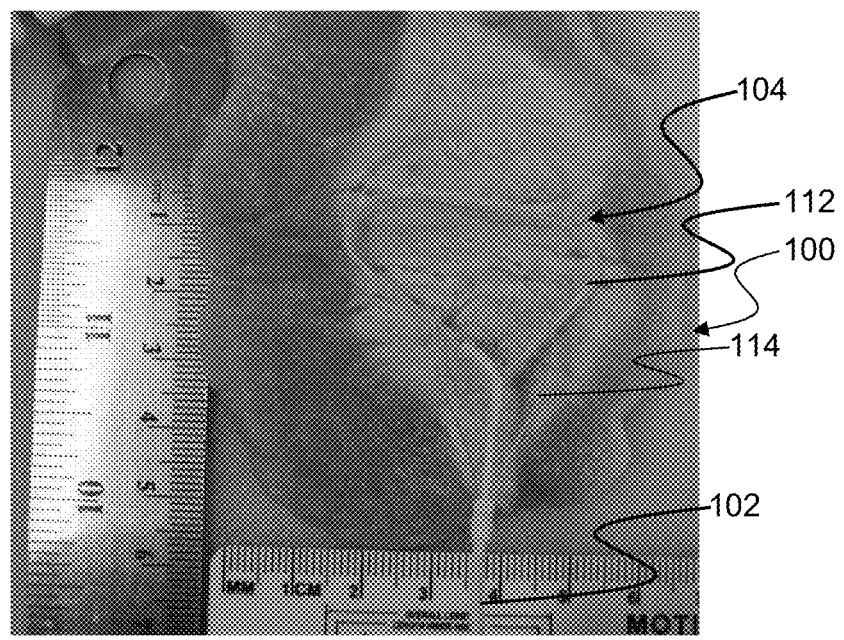
FIG. 6D shows the unfolded piece of tissue of FIG. 6C showing the placement of the microwave antenna of FIGS. 6A and 6B in a longitudinally constrained and laterally un-collapsed working configuration and the ablation obtained from the microwave antenna.

FIG. 6D shows the unfolded piece of tissue of FIG. 6C showing the placement of the microwave antenna of FIGS. 6A and 6B in a longitudinally constrained and longitudinally collapsed working configuration and the ablation obtained from the microwave antenna. It should be noted that the ablation is roughly triangular in shape. Such an ablation in the uterus is capable of ablating the entire uterine endometrium to treat menorrhagia without the need of repositioning antenna 104.

Figure 6E:
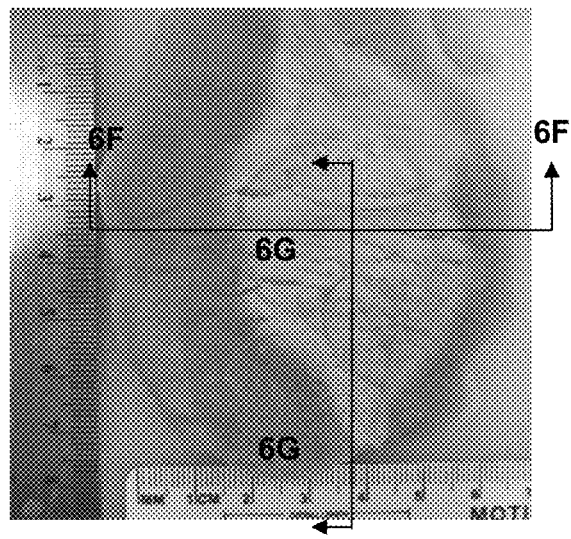
FIG. 6E shows an unfolded view of ablated tissue after the ablation shown in FIG. 6C.
Figure 6F:
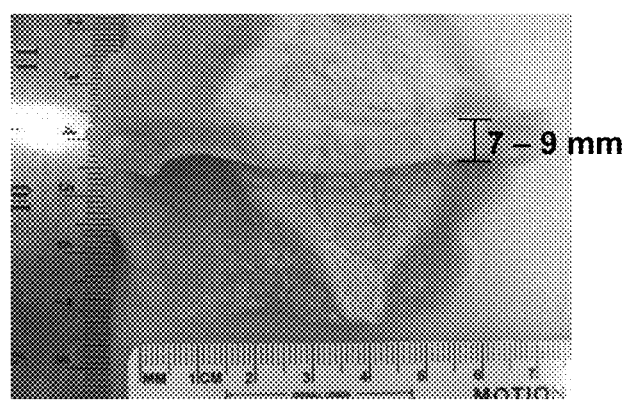
FIG. 6F shows a view of the ablated tissue sliced through the plane 6F-6F in FIG. 6E.
Figure 6G:
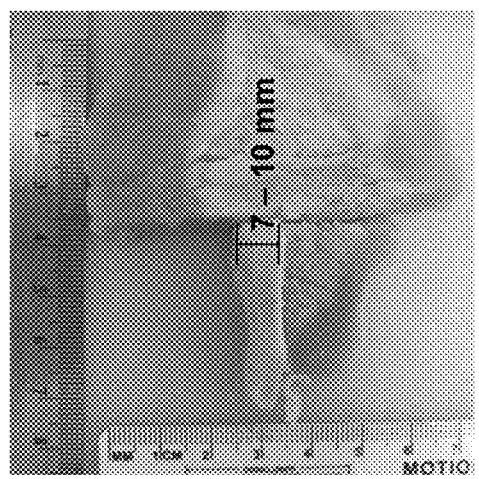
FIG. 6G shows a view of the ablated tissue sliced through the plane 6G-6G in FIG. 6E.

FIG. 6E shows an unfolded view of ablated tissue after the ablation shown in FIG. 6C. FIG. 6F shows a view of the ablated tissue sliced through the plane 6F-6F in FIG. 6E. It is seen in FIG. 6F, that the ablation is uniform and spans the full thickness of the tissue. There is no charring noted anywhere. Thus a transmural ablation spanning the full 7-9 mm depth of tissue has been created. FIG. 6G shows a view of the ablated tissue sliced through the plane 6G-6G in FIG. 6E. Similar to FIG. 6F, FIG. 6G shows that the ablation is uniform and spans the full thickness of the tissue. There is no charring noted anywhere. Thus a transmural ablation spanning the full 7-10 mm depth of tissue has been created. Further, it should be noted that the lesion is deeper in the center and shallower towards the periphery of the lesion.

Such an ablation is clinically desired since the thickness of the endometrium is greater toward the center of the uterus and is lower in the cornual regions and towards the lower uterine region. Further, deeper lesions may be created if desired by using one or more of: increasing the power delivered by the microwave generator, increasing the ablation time, occluding the blood flow to the uterus by temporarily occluding the uterine arteries, etc. Further, shallower lesions may be created if desired by using one or more of: reducing the power delivered by the microwave generator, reducing the ablation time, using a cooling modality such as a circulating cooling agent in the anatomy, etc. A cooling modality may be used to cool the surface of the endometrium.

Further, such a deep ablation of tissue enables ablation device 100 to be used for endometrial ablation without any pre-treatment of the endometrium. Several of the prior art endometrial ablation techniques require pre-treatment of the endometrium to thin the endometrium. For example, Dilatation & Curettage (D&C) or hormonal pre-treatment is necessary before using several of the prior art techniques. This drives up the overall cost and complexity of the treatment process. Further, hormonal pre-treatment is not readily accepted by the patients because of the potential for unpleasant side effects. The deep lesion created by the devices and methods disclosed herein may easily be used for endometrial ablation without needing any pre-treatment. Further, such a deep ablation of tissue enables the devices and methods disclosed herein to be used at any time during the menstrual cycle.

The maximum tissue temperature measured during the ablation was 85 degrees C. Thus, there is no risk of charring of tissue. Further, this eliminates the formation of steam during the ablation. This in turn eliminates the medical risks due to steam formation. Steam generated during the ablation dissipates heat and also carries the risk of burning healthy tissue. It should also be noted that antenna 104 did not stick or adhere to the tissue. This is critical since ablation device 100 will have none or minimal risk of sticking to uterine tissue when used for endometrial ablation.

Figure 7A:
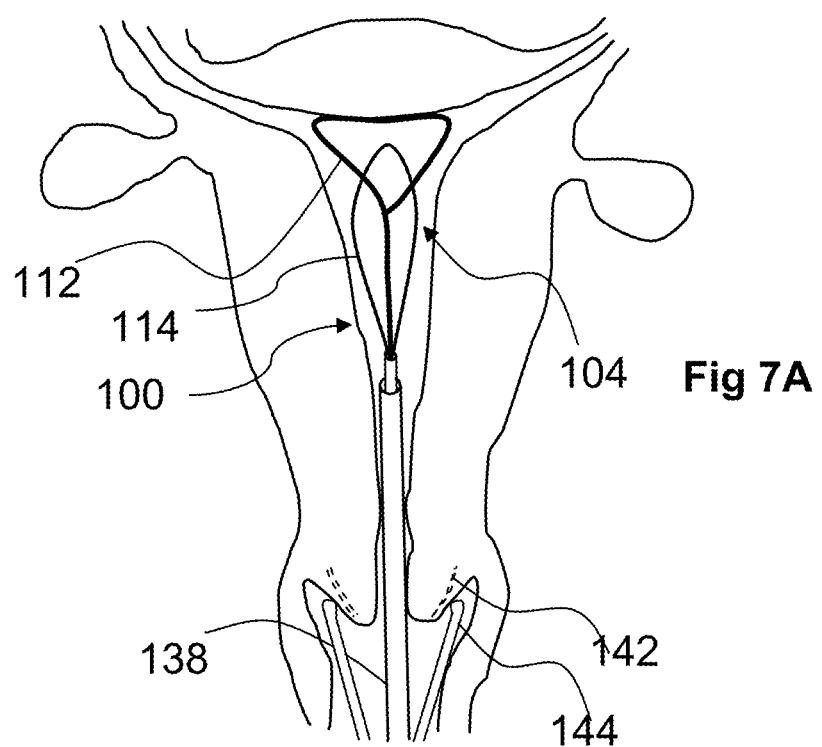
FIGS. 7A and 7B illustrate two steps of a method of endometrial ablation with a reduced uterine blood flow.
Figure 7B:
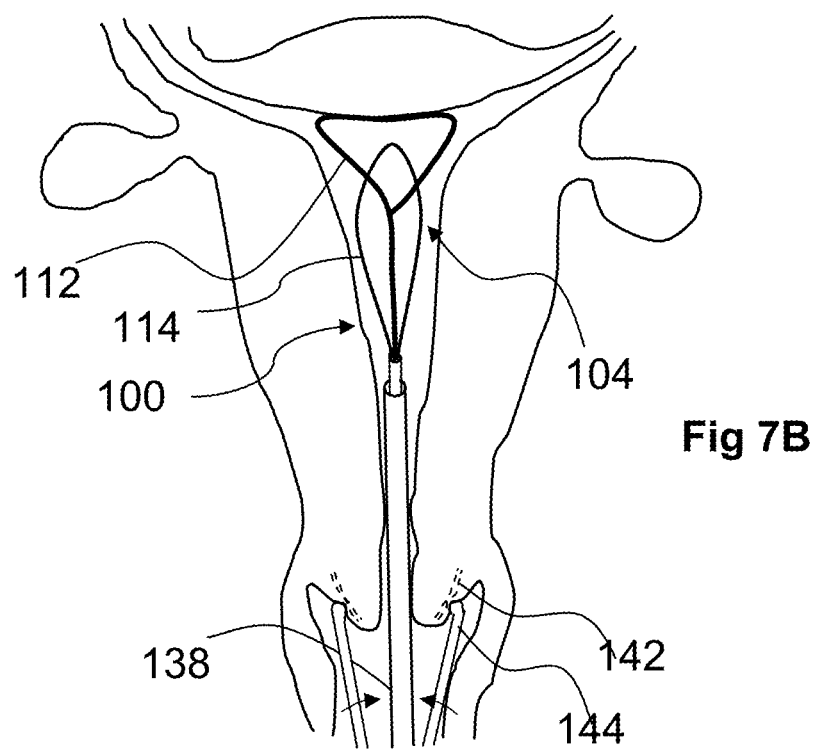

One or more of the endometrial ablation methods disclosed herein may be combined with occlusion of uterine arteries to increase the efficacy and/or increase the safety of the endometrial ablation methods. One of the factors that reduce the efficacy of some existing endometrial ablation techniques is blood flow in the uterus. The blood flow acts as a heat sink and carries away the heat delivered to the uterus. Thus, if a thermal endometrial ablation method is performed while reducing the uterine blood flow; a beneficial effect may be obtained. FIGS. 7A and 7B illustrate two steps of a method of endometrial ablation with a reduced uterine blood flow. In FIGS. 7A and 7B, uterine arteries 142 are occluded. The occlusion is temporary and is created by a clamp 144 that is inserted through the vagina and is used to compress the external surface of the cervix to compress and occlude the uterine arteries 142. Alternately, a permanent occlusion of the uterine arteries 142 may be used. The uterine artery occlusion may be partial or complete. In one embodiment, the location of the uterine arteries 142 and/or the magnitude of the blood flow in the uterine arteries is determined by using Doppler ultrasound or other ultrasound modality. Similar endometrial ablation methods are contemplated that use an existing endometrial ablation modality such as hot liquid balloons, free circulating hot liquids, etc. in conjunction with temporary or permanent uterine artery occlusion. In such endometrial ablation methods, the amount of thermal energy delivered to the endometrium may be reduced as compared to similar endometrial ablation methods that do not use uterine artery occlusion. Treatment protocols may be designed that deliver a lower amount of thermal energy to the uterine. Alternately, the amount of thermal energy delivered to the endometrium may be kept the same.

Figure 8A:
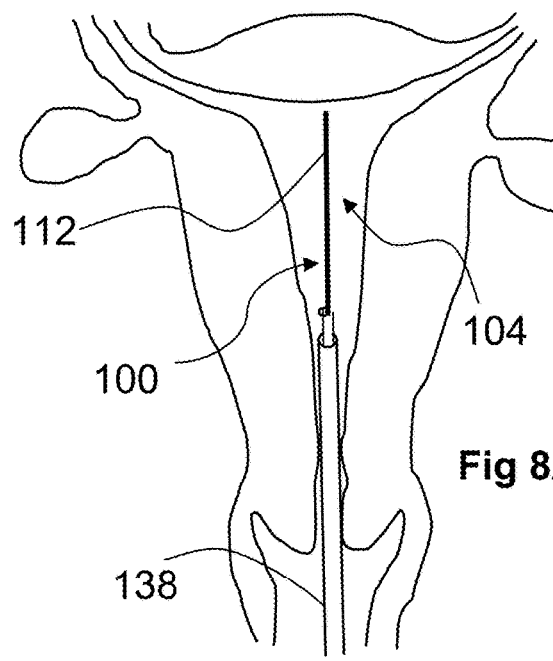
FIGS. 8A-8C show the steps of a method of using an ablation device 100 with a deflectable or steerable antenna 104 being used for endometrial ablation.
Figure 8B:
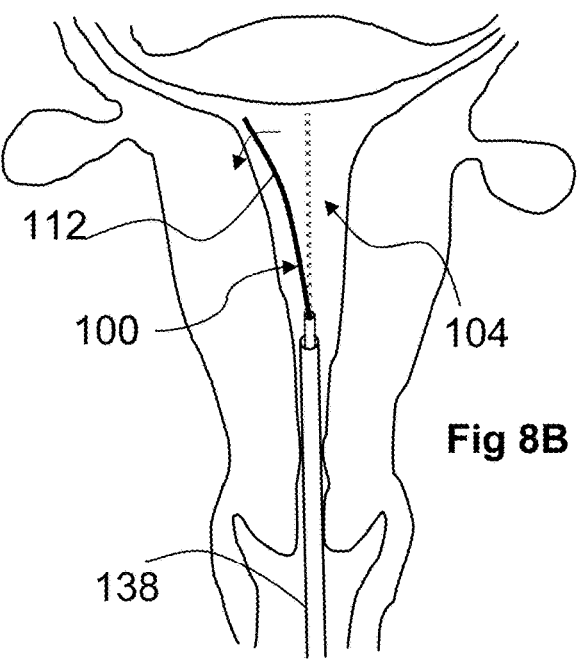
Figure 8C:
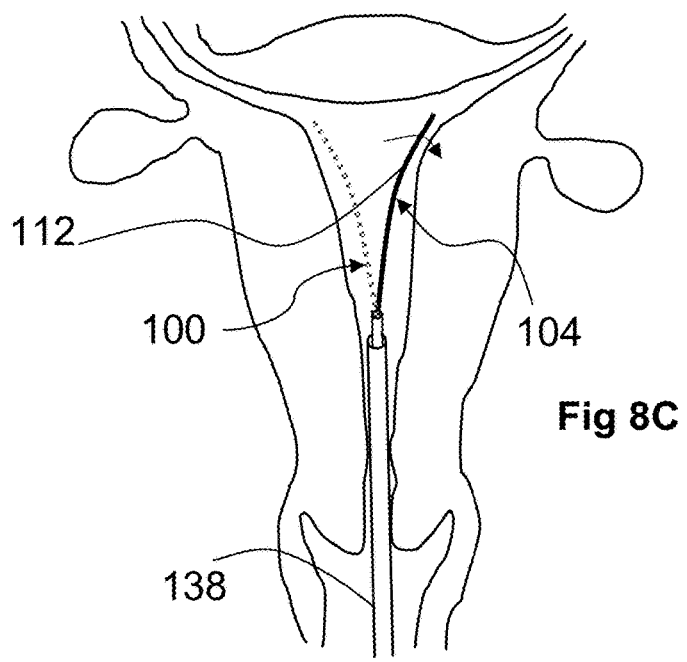

Although several embodiments of ablation devices 100 have been disclosed herein that are capable of ablating the entire anatomical target in a single ablation without repositioning antenna 104, several device and method embodiments are envisioned wherein antenna 104 is re-positioned at least once to ablate multiple locations in the anatomical target. For example, endometrial ablation methods may be designed wherein antenna 104 is positioned at a first location in the uterine cavity and is used to ablate the first location in the uterine cavity. Thereafter, antenna 104 is positioned at a second location in the uterine cavity and is used to ablate the second location in the uterine cavity. Thereafter, if needed, antenna 104 may be repositioned at additional locations in the uterine cavity and used to ablate the additional locations in the uterine cavity. FIGS. 8A-8C show the steps of a method of using an ablation device 100 with a deflectable or steerable antenna 104 being used for endometrial ablation. In FIG. 8A, an ablation device 100 comprising antenna 104 is introduced trans-cervically into the uterine cavity. Although in the embodiment shown in FIG. 8A, antenna 104 comprises a radiating element 112 (e.g. a monopole antenna, a helical antenna, outer loop 112 of FIG. 1, etc.) without any shaping element, one or more conducting or non-conducting shaping elements 114 may be added to antenna 104 to shape the microwave field. In the embodiment in FIG. 8A, the length of antenna 104 is greater than half of the uterine cavity length. Antenna 104 is positioned such that the distal end of antenna 104 is in the vicinity of the uterine fundus. In FIG. 8A, antenna 104 is used to ablate a region of the uterine endometrium. Thereafter, in FIG. 8B, antenna 104 is moved to a different location in the uterus and antenna 104 is used to ablate a region of the uterine endometrium. In one embodiment, a deflecting or steering mechanism on ablation device 100 is used to displace antenna 104. Examples of such deflecting or steering mechanisms include, but are not limited to: pull wires, balloons and magnetic steering. The steering mechanisms such as pull wires may be designed such that there is none or minimal interaction of the steering mechanisms with the microwave field. In one embodiment, the deflecting or steering mechanisms are made of non-conductive materials. Thereafter, in FIG. 8C, antenna 104 is moved to another location in the uterus and antenna 104 is used to ablate a region of the uterine endometrium. Similar to the step in FIG. 8B, a deflecting or steering mechanism on ablation device 100 may be used to displace antenna 104. The ablations created in the steps in FIGS. 8A, 8B and 8C may be overlapping or non-overlapping. The ablations created in the steps in FIGS. 8A, 8B and 8C may be shaped to be wider distally and narrower proximally in the uterine cavity. In one alternate embodiment, the ablations created in the steps in FIGS. 8A, 8B and 8C may have a substantially constant width along their length. Antenna 104 in FIGS. 8A, 8B and 8C may be substantially flexible or substantially non-flexible. The displacement of antenna 104 may be performed by a controller coupled to a proximal portion of ablation device 100. The controller may be mechanical and/or electromechanical.

Figure 8D:
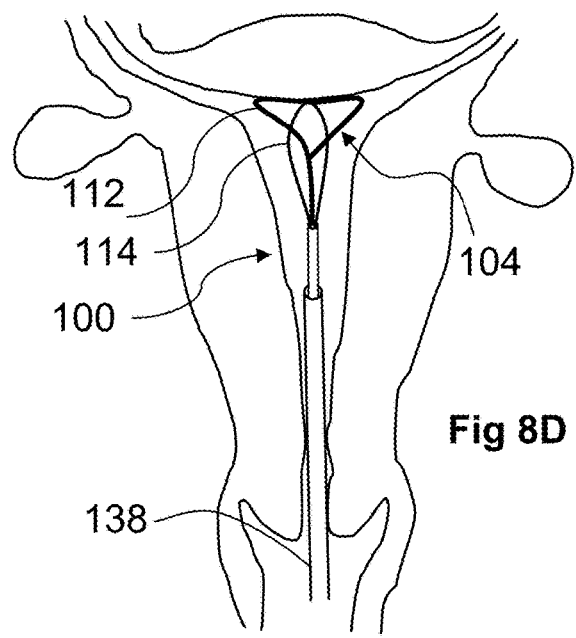
FIGS. 8D-8E show a method embodiment of treating a uterine cavity by ablating a distal and a proximal region of the uterine cavity in two separate ablations.
Figure 8E:
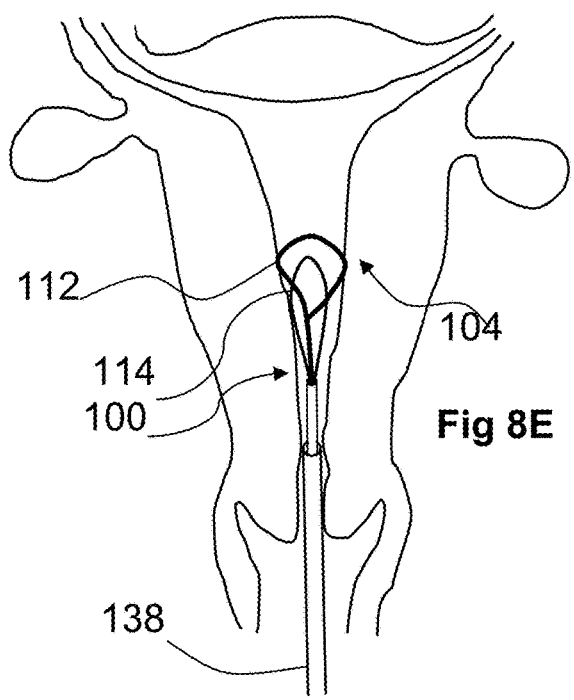

Antenna 104 may be repositioned at multiple regions in the target tissue with or without using a deflecting or steering mechanism on ablation device 100 to ablate a larger region of the target tissue. A physician controlled movement of the ablation device 100 may be used to reposition antenna 104. Two or more ablations may thus be created that may or may not overlap with each other. For example, FIGS. 8D-8E show a method embodiment of treating a uterine cavity by ablating a distal and a proximal region of the uterine cavity in two separate ablations. Such methods may be used for treating a uterus with a normal cavity or a large uterus (e.g. having a uterine cavity of >8 cm in length). Such methods also allow the use of a smaller antenna 104 that can be repositioned one or more times to ablate a larger region of target tissue. In FIG. 8D, antenna 104 is used to ablate a distal region in the uterine cavity. In one device embodiment, center loop 114 is stiffer than outer loop 112. Ablation device 100 is advanced into the uterine cavity such that the distal region of outer loop 112 touches the fundus and is distorted by the fundus as shown in FIG. 8D. Ablation device 100 is further advanced into the uterine cavity such that the distal region of center loop 114 touches a portion of the uterine cavity. The user feels the increased resistance and stops advancing ablation device 100 further into the uterine cavity. Thus, the user gets a tactile feedback about the accurate positioning of antenna 104 inside the uterine cavity. In another embodiment, a stopper located on either of introducing sheath 138 or coaxial cable 102 is used to position antenna 104 accurately in the uterine cavity. The stopper may be designed such that it abuts against the external region of the cervix and prevents further advancement of ablation device 100. The location of the stopper along ablation device 100 may be adjustable. The location of the stopper along ablation device 100 may be adjusted based on anatomical data obtained before the ablation. Thereafter, in FIG. 8E, antenna 104 is repositioned to a proximal location in the uterine cavity. Thereafter, a second ablation is carried out. Thus, several ablation protocols may be designed that direct the user to place antenna at pre-specified locations in the uterine cavity. These protocols may be based on one or more of: tactile feedback, pre-procedure imaging, anatomical dimensions (length and position of the uterine cavity, length and position of the cervical canal, width of the uterine cavity, uterine cavity shape, etc.) obtained before an ablation, intra-procedure imaging, location of anatomical landmarks, location of device landmarks and intra-procedure feedback (e.g. temperature feedback, impedance feedback). Such protocols differ from prior art endometrial ablation protocols such as Microwave Endometrial Ablation of Microsulis Medical Ltd. that are based solely on temperature feedback. The methods herein may be used to ablate the entire or a part of (e.g. about 50% or about 75%) the endometrium. The methods herein may be used to increase procedural safety e.g. by preventing any ablation of the cervical canal. The shapes of antenna 104 in FIGS. 8D and 8E may or may not be the same because of differing distortions to antenna 104 by the anatomy. Any of the antennas 104 disclosed herein may be repositioned by one or more of: rotating around an axis, moving proximally or distally, moving sideways, revolving around an axis, increasing or reducing in size, engaging a steering or deflecting mechanism on ablation device 100 and engaging a steering or deflecting mechanism on an accessory device. Further, any of the antennas 104 disclosed herein may be designed and used such that during clinical use the forces exerted by a flexible antenna 104 on the uterine wall do not distort the uterine cavity.

Figure 9:
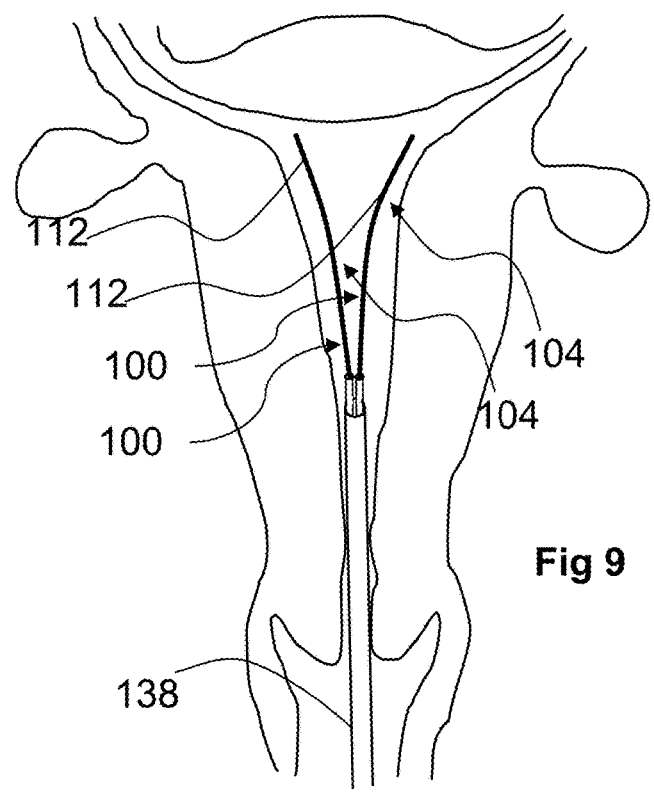
FIG. 9 shows a method of simultaneously using two ablation devices 100 to ablate the uterine endometrium.

Multiple antennas 104 located on one or more ablation devices 100 may be used to ablate one or more regions of the anatomy. For example, FIG. 9 shows a method of simultaneously using two ablation devices 100 to ablate the uterine endometrium. In this embodiment, two ablation devices 100 each comprising a single antenna 104 are used to ablate the uterine endometrium. Alternately, more than two ablation devices 100 may be used to ablate the uterine endometrium. The ablation devices 100 in FIG. 9 may comprise a deflecting or steering mechanism to displace antenna 104. The ablations created by ablation devices 100 in FIG. 9 may be overlapping or non-overlapping. The ablations created by ablation devices 100 in FIG. 9 may be created simultaneously or sequentially. Ablation devices 100 in FIG. 9 may be supplied by a single energy source e.g. a single generator or multiple energy sources e.g. multiple generators. In other embodiments, an ablation device 100 comprising two or three or more antennas 104 is used to ablate a target tissue.

One or more devices disclosed herein may comprise one or more ultrasound imageable and/or radiopaque components. One or more devices disclosed herein may comprise one or more lubricious coatings. One or more devices disclosed herein may comprise one or more regions that are thermally insulated to protect non-target tissue. One or more devices disclosed herein may comprise a torqueable shaft and a proximal orientation marker. For example, ablation device 100 may comprise a torqueable shaft and a proximal hub with wings. The user can thus determine the orientation of the antenna 104 within the body by knowing the orientation of the wings of the proximal hub that lie outside the body.

Figure 10A:
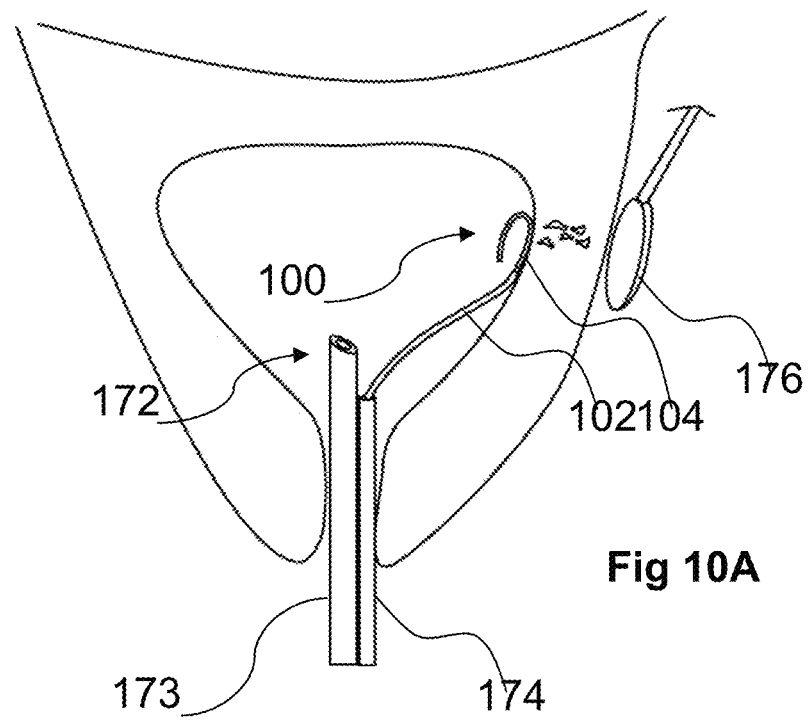
FIGS. 10A and 10B show two methods of using a trans-cervical access device in combination with a energy emitting device to treat a local region of the uterus.
Figure 10B:
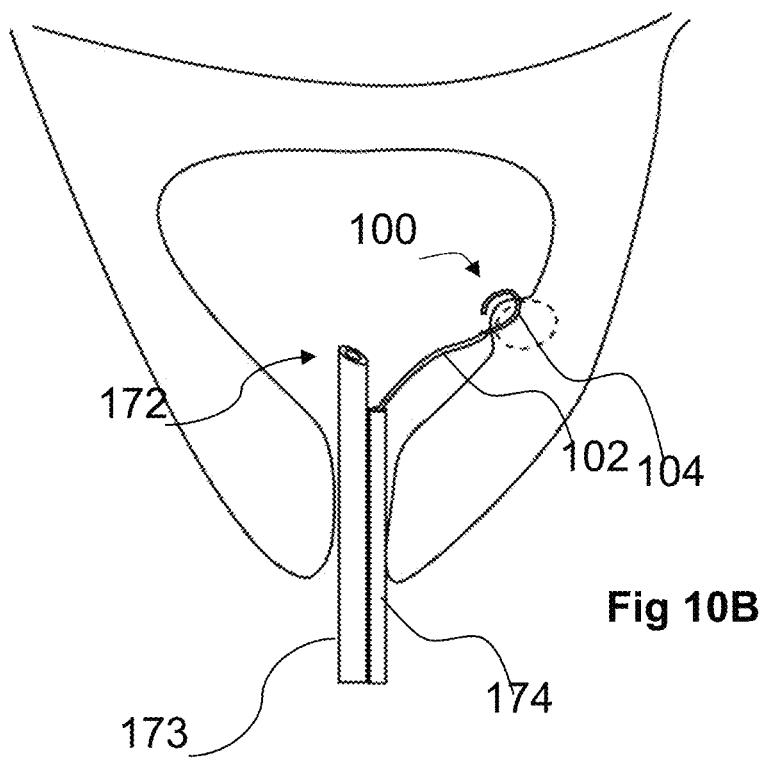

FIGS. 10A and 10B show two methods of using a trans-cervical access device in combination with a energy emitting device to treat a local region of the uterus. In FIGS. 10A and 10B, an access device is used to create an access to the uterine cavity. Thereafter, a working device e.g. an ablation device 100 is inserted inside the uterine cavity using the access device. Thereafter, the working device is used to perform a diagnostic or therapeutic procedure on one or more regions of the uterus. In FIG. 10A, the access device is a hysteroscope sheath 173 comprising a device lumen 174. A hysteroscope 172 enclosed within hysteroscope sheath 173 is introduced inside the uterine cavity. Hysteroscope 172 may be used to guide the introduction and placement of the working device such as an ablation device 100. The cervix may then be sealed to create a fluid tight seal to enable a distension medium to be used to distend the uterine cavity. In one device embodiment, the access device e.g. hysteroscope sheath 173 has one or more openings on its surface that are positioned in the cervical canal. Thereafter, suction applied through the one or more openings collapses the cervical canal tissue over the access device thereby sealing the cervix. In FIG. 10A, the working device is an ablation device 100 designed for ablating portions of the uterine wall. After ablation device 100 is inserted inside the uterine cavity, antenna 104 of ablation device 100 may be deployed and positioned adjacent to the target tissue. A shield 176 may be positioned outside the uterus to protect abdominal organs from the energy delivered by ablation device 100. The access device and/or working device may be used to generate a vacuum in the uterine cavity to remove any gases, debris, moisture, etc. The access device and/or working device may be used to deliver local anesthetic inside the uterine cavity. Ablation device 100 may be used to ablate one or more regions of the uterine wall to treat local lesions such as adenomyosis, polyps, uterine cancer, hyperplasia, etc or to globally ablate the endometrium. A chemical or mechanical pre-treatment of a uterine region may be performed before a procedure. After the procedure is complete, an intervention to prevent adhesions in the uterine cavity may be performed e.g. by inserting a packing material.

Thereafter, the working device and access device are removed from the anatomy. FIG. 10B shows a variation of the method of FIG. 10A wherein antenna 104 is used to treat a sub-mucous fibroid. In one embodiment, the entire volume of the fibroid is treated. In another embodiment, the endometrium covering the fibroid is treated.

Even though antenna 104 is designed to work well without exact contact with tissue, there may be an advantage if the proper positioning of the antenna 104 is determined just before the ablation. The invention herein further includes a non-visual and integrated device that can be used to determine the proper positioning of antenna 104 just before the ablation. The method uses reflectometry to determine the proper positioning. If the antenna is not properly positioned, the antenna may not be well matched. In such a case, the measured reflected power for a particular range of incident power (the power sent to the antenna) will not be within a normal range. Thus by measuring if the reflected power is within a normal range, we can say whether the antenna is properly positioned. An example of such a procedure is as follows. 1. Conduct a series of experiments with the antenna properly positioned in the target tissue, 2. Measure the reflected power level in all the experiments for a particular range of incident power level with the antenna properly positioned in the target tissue, 3. Determine a "normal range" of reflected power level that is to be expected if the antenna is properly positioned in the target tissue, 4. During the endometrial ablation procedure, measure the reflected power level, 5. If the reflected power level is within the normal range, conclude that the antenna is properly positioned. If the reflected power level is not within the normal range, conclude that the antenna is not properly positioned. As an optional extra step, a series of experiments may be conducted with the antenna improperly positioned in the target tissue by having the antenna deployed purposely in imperfect or wrong configuration. This is to determine an "abnormal range" of incident power level that is to be expected if the antenna is not properly positioned in the target tissue.

The reflected power level can be measured by 1. using an external power meter or 2. using a power meter that is in-built within the microwave generator.

The devices and methods disclosed herein may also be used to treat Dysmenorrhea. Reduction in Dysmenorrhea has been clinically documented after endometrial ablation. In one method embodiment, one or more of the methods and devices disclosed herein may be used to treat concomitant Dysmenorrhea and menorrhagia.

The microwave field generated by any antenna 104 disclosed herein may be directed towards a particular direction by a variety of mechanisms. For example, a microwave reflector (e.g. a metallic mesh) may be positioned on one side of a flat or planar ablation portion to reflect the microwave energy to the other side of the flat or planar ablation portion. One or more microwave absorbing or shielding or reflecting materials may be used in combination with the embodiments disclosed herein to direct the microwave field to a particular direction. In one embodiment, the whole or part of center loop 114 is designed to act as a microwave shield or reflector or absorber.

Some of the embodiment of ablation device 100 such as in FIG. 1A may be broadly described as microwave devices comprising a coaxial cable and an antenna at the distal end of the coaxial cable. The antenna comprises a radiating element that extends from the distal end of the coaxial cable. For example, the radiating element may be a continuation of the inner conductor of the coaxial cable or may be an additional element connected to the inner conductor of the coaxial cable. The radiating element radiates a microwave field that is characteristic of its specific design. The radiated microwave field causes agitation of polarized molecules, such as water molecules, that are within target tissue. This agitation of polarized molecules generates frictional heat, which in turn raises the temperature of the target tissue. Further, the microwave field radiated by the radiating element may be shaped by one or more shaping element(s) in the antenna. The shaping element(s) may be electrically connected to the outer conductor of the coaxial cable. Several embodiments of the radiating element and the shaping element and combinations thereof are described herein. A significant portion of the disclosure discloses embodiments of ablation devices, wherein the radiating element is substantially a loop and the shaping element is substantially a loop. Although a significant portion of the disclosure discloses such embodiments of ablation devices, the invention also includes other embodiments of ablation devices and methods of using such devices. For example, one or both of outer loop 112 and center loop 114 may be replaced by one or more non-looped conducting, non-conducting or insulated elements. Examples of such elements include, but are not limited to: straight or curved segments of metallic elements, elements with a circular or oval shape, elements with a polygonal shape (e.g. triangular, square, rectangular, pentagonal, etc.), multiple elements joined together by an electrically conducting joint(s), multiple elements joined together by a non-electrically conducting joint(s), elements with multiple curves, symmetrically arranged segments of elements, non-symmetrically arranged segments of elements, segments of non-conducting materials, etc.

Several embodiments of antennas 104 may be designed to have single or multiple splines, curves or loops in a generally planar arrangement. This is advantageous in ablating a surface such as the surface of organs such as liver, stomach, esophagus, etc.

Devices disclosed herein may be constructed with various orientations of the antenna 104 relative to the region of coaxial cable 102 immediately proximal to antenna 104. Devices herein may be designed with a planar antenna 104 that is substantially parallel to the region of coaxial cable 102 immediately proximal to antenna 104. Devices can also be designed with a planar antenna 104 oriented at an angle (e.g. 90+/−20 degrees, 45+/−20 degrees) to the region of coaxial cable 102 immediately proximal to antenna 104. This is advantageous to reach hard-to-reach target regions in the body. The relative orientation of whole or portions of antenna 104 relative to the device shaft (e.g. the coaxial cable 102) may be fixed or changeable. For example, there may be a springy joint or region between antenna 104 and the shaft. In another embodiment, there may be an active steering mechanism e.g. a pull wire mechanism to change the relative orientation of whole or portions of antenna 104 relative to the shaft. Such mechanisms may be used for proper positioning of antenna 104 on the target tissue or for navigating the device through the anatomy. For example, an antenna 104 deployed through an endoscope or through a laparoscope port may be deployed and navigated such that antenna 104 lies in the plane of the target tissue.

The user may be supplied several devices of varying size and/or shape. The user may then select the proper device based on his judgment to carry out the ablation. In a particular embodiment, 2 to 3 different devices with antennas 104 of similarly shape but different sizes are supplied. The user then selects the proper device. Such multiple devices may be packaged separately or together. In another embodiment, 2 to 3 different devices with antennas 104 of similarly sizes but different shapes are supplied. The user then selects the proper device. In an alternate embodiment, the deployment of the device is tailored to the particular target tissue or cavity. In such embodiments, whole or parts of antenna 104 is designed to be deployed in a particular size and/or shape that best fits the particular target tissue or cavity.

Any of the antennas 104 disclosed herein may or may not lie in the plane of the distal region of coaxial cable 102. For example, in FIG. 1A, ablation device 100 may be pre-shaped such that antenna 104 lies in the plane of the distal region of coaxial cable 102. In an alternate embodiment, antenna 104 is oriented at an angle to the plane of the distal region of coaxial cable 102. For example, antenna 104 may be oriented at an angle ranging from about 20 degrees to about 90 degrees to the plane of the distal region of coaxial cable 102. The orientation of antenna 104 relative to the orientation of the distal region of coaxial cable 102 or the shaft of ablation device 100 may be relatively constant or may be adjustable by the user. In one such embodiment, ablation device 100 is provided with a deflecting or steering mechanism to controllably change the orientation of antenna 104 relative to the orientation of the distal region of coaxial cable 102 or the shaft of ablation device 100.

In any of the devices disclosed herein, instead of coaxial cable 102, an alternate element for transmitting microwaves may be used. Examples of such alternate elements for transmitting microwaves include, but are not limited to: waveguides, micro strip lines, strip lines, coplanar waveguide and rectax. In such embodiments, shaping element 114 may be electrically connected to a portion of the shielding element of the transmission line. In a coaxial cable, the shielding element is the outer conductor. In a strip line, wherein the shielding element is the combination of the two ground planes, shaping element(s) 114 may be in electrical conduction with the combination of the two ground planes. In a hollow metallic waveguide, wherein the shielding element is the electrically conducting wall, shaping element (s) 114 may be in electrical conduction with the electrically conducting wall.

Any of the devices disclosed herein may comprise an impedance and/or temperature measuring modality. In one embodiment, a device disclosed herein comprises a radiometric temperature sensing modality. This radiometric temperature sensing modality may be used to non-invasively measure of temperature at the surface or at a deeper region of tissue. This in turn can be used to obtain real-time feedback about the effectiveness of energy delivery by the device.

One or more elements described herein may comprise one or more additional treatment modalities. Examples of such additional treatment modalities include, but are not limited to: radiofrequency electrodes including radiofrequency ablation electrodes, heating elements, cryotherapy elements, elements for emitting laser and other radiation, elements for introducing one or more fluids, etc. For example, outer loop 112 and/or center loop 114 may comprise multiple radiofrequency ablation electrodes. Such radiofrequency ablation electrodes enable the use of the devices disclosed herein in conjunction with other modalities such as radiofrequency ablation. One or more elements described herein may comprise one or more additional diagnostic modalities. Examples of such diagnostic modalities include, but are not limited to: temperature sensors, impedance sensors, electrophysiological signal sensors, visualization elements, etc. For example, outer loop 112 and/or center loop 114 may comprise multiple temperature sensors.

In addition to endometrial ablation, the devices and methods disclosed herein may be used for liver ablations for treating liver tumors, skin ablations for treating wrinkles, cardiac tissue ablations for treating atrial fibrillation, Ventricular Tachycardia, Bradycardia and other arrhythmias. The devices and methods disclosed herein may be used for deeper heating to cause tissue shrinkage for treating conditions such as fecal incontinence, GERD, urinary incontinence, etc. Such deeper heating may be carried out within lumens or other bodily cavities.

Various additional embodiments of antenna 104 may be designed wherein the radiating element is a straight or curved or bent or pre-shaped monopole antenna.

Several examples or embodiments of the invention have been discussed herein, but various modifications, additions and deletions may be made to those examples and embodiments without departing from the intended spirit and scope of the invention. Thus, any element, component, method step or attribute of one method or device embodiment may be incorporated into or used for another method or device embodiment, unless to do so would render the resulting method or device embodiment unsuitable for its intended use. If the various steps of a method are disclosed in a particular order, the various steps may be carried out in any other order unless doing so would render the method embodiment unsuitable for its intended use. Various reasonable modifications, additions and deletions of the described examples or embodiments are to be considered equivalents of the described examples or embodiments.

We claim:

1. A method of delivering energy to a target tissue using a microwave generator, the method comprising:
   inserting a microwave ablation device into a cavity and adjacent to a surface of the target tissue, where the microwave ablation device comprises a flexible microwave antenna that is electrically connected to the microwave generator;
   changing a shape of the flexible microwave antenna within the cavity;
   positioning the flexible microwave antenna adjacent to a desired region of the target tissue without penetrating the target tissue;
   applying microwave energy to the flexible microwave antenna; and
   using reflectometry based on microwave energy supplied to the flexible microwave antenna to determine a position of the flexible microwave antenna at the desired region of target tissue.

2. The method of delivering energy of claim 1, where using reflectometry comprises determining if a measured reflected power is within a predetermined range.

3. The method of delivering energy of claim 1, where using reflectometry comprises measuring a plurality of reflected power levels with the flexible microwave antenna positioned at the target tissue.

4. The method of delivering energy of claim 3, further comprising improperly positioning the flexible microwave antenna at the target tissue and measuring the plurality of reflected power levels with the flexible microwave antenna improperly positioned at the target tissue.

5. The method of delivering energy of claim 3, further comprising positioning the flexible microwave antenna properly at the target tissue and measuring the plurality of reflected power levels.

6. The method of delivering energy of claim 1, wherein using reflectometry comprises measuring a reflected power level using an external power meter.

7. The method of delivering energy of claim 1, wherein using reflectometry comprises measuring a reflected power level using a power meter in-built within the microwave generator.

\* \* \* \* \*